United States Patent [19]

Epstein et al.

[11] 4,435,419

[45] Mar. 6, 1984

[54] METHOD OF TREATING DEPRESSION USING AZABICYCLOHEXANES

[75] Inventors: Joseph W. Epstein, Monroe; Arnold C. Osterberg, Pearl River; Herbert J. Brabander, Nanuet, all of N.Y.

[73] Assignee: American Cyanamid Company, Stamford, Conn.

[21] Appl. No.: 376,131

[22] Filed: May 10, 1982

Related U.S. Application Data

[63] Continuation-in-part of Ser. No. 279,366, Jul. 1, 1981, abandoned.

[51] Int. Cl.³ .................... A61K 31/40; C07D 209/52
[52] U.S. Cl. .................................. 424/274; 548/452; 548/454
[58] Field of Search ................ 424/274; 548/452, 454

[56] References Cited

U.S. PATENT DOCUMENTS 4,131,611 12/1978 Fanshawe et al. ................ 424/274

OTHER PUBLICATIONS

Epstein et al., J. Med. Chem., 24:481 (1981).

*Primary Examiner*—Stanley J. Friedman
*Attorney, Agent, or Firm*—Edward A. Conroy, Jr.

[57] ABSTRACT

The present invention concerns certain novel substituted 3-azabicyclo[3.1.0]hexanes and a method of treating depression and stress in a warm-blooded animal, comprising the administration of substituted 3-azabicyclo[3.1.0]hexanes.

24 Claims, No Drawings

METHOD OF TREATING DEPRESSION USING AZABICYCLOHEXANES

CROSS-REFERENCE TO RELATED APPLICATIONS

This application is a continuation-in-part of copending application Ser. No. 279,366, filed July 1, 1981, now abandoned.

BACKGROUND OF THE INVENTION

1. Field of Invention

This invention relates to certain novel substituted 3-azabicyclo[3.1.0]hexanes and to compositions of matter containing said novel compounds.

This invention further relates to a novel method of treating depression and stress in warm-blooded animals, and particularly to a method of treating depression and stress by the administration of substituted 3-azabicyclo[3.1.0]hexanes.

2. Prior Art

The 3-azabicyclo[3.1.0]hexanes of Formulas II, III, IV, and V below are disclosed in U.S. Pat. No. 4,131,611, incorporated herein by reference, where their utility is given as anxiolytic and analgesic agents. See also J. W. Epstein et al., "1-Aryl-3-azabicyclo[3.1.0]hexanes, a New Seris of Nonnarcotic Analgesic Agents", J. Med. Chem. 24: 481(1981), incorporated herein by reference.

SUMMARY OF THE INVENTION

This invention concerns novel optically active compounds of the following formula:

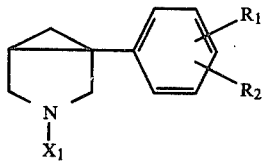

(I)

wherein
$X_1$ is hydrogen or a radical of the formula:

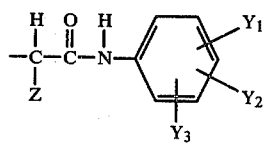

(IA)

wherein Z is $C_1-C_6$ alkyl and $Y_1$, $Y_2$ and $Y_3$ are each independently selected from the group consisting of hydrogen, halo and $C_1-C_6$ alkyl;

$R_1$ and $R_2$ are each independently selected from the group consisting of hydrogen, halo, $C_1-C_6$ alkanoyl, $C_1-C_6$ alkylamino, di-$C_1-C_6$-alkylamino, a radical of the formula:

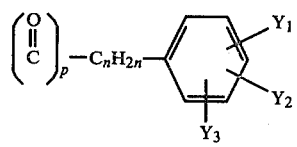

(IB)

wherein n is an integer 0 to 2 and p is an integer 0 or 1, with the proviso that n and p cannot both be 0, and $Y_1$, $Y_2$, and $Y_3$ are as defined above; and a radical of the formula:

(IC)

wherein W is hydrogen or $C_1-C_5$ alkyl;

or $R_1$ and $R_2$ taken together are methylenedioxy; with the proviso that when $X_1$ is hydrogen, $R_1$ and $R_2$ cannot both be hydrogen and neither $R_1$ nor $R_2$ can be halo; the racemic mixture thereof; the mirror image thereof; and the non-toxic pharmaceutically acceptable salts thereof.

The present invention is also concerned with compositions of matter containing compounds of Formula I.

This invention is further concerned with a method of treating depression and stress in warm-blooded animals using the novel compounds of Formula I above and also using the known, optically active compounds of the following formulas II–VI:

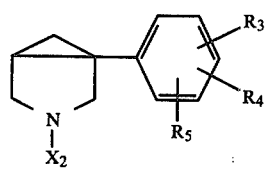

(II)

wherein $R_3$, $R_4$, and $R_5$ are each independently selected from the group consisting of hydrogen, halo, $C_1-C_6$ alkyl, $C_1-C_6$ alkoxyl, trifluoromethyl, nitro, amino, acetamido and hydroxyl; $X_2$ is selected from the group consisting of hydrogen, $C_1-C_8$ alkyl, and a moiety of the formula $C_mH_{2m}A$, wherein m is an integer from 0 to 3 and A is selected from the group consisting of phenyl, halophenyl, naphthyl, norbornenyl, adamantyl, and p-fluorobenzyl; the racemic mixture thereof; the mirror image thereof; and the non-toxic pharmaceutically acceptable salts thereof;

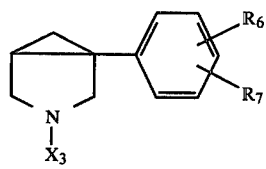

(III)

wherein $R_6$ and $R_7$ are each independently selected from the group consisting of hydrogen, phenyl, halophenyl, $C_1-C_6$ alkoxymethyl, and $C_3-C_6$ cycloalkyl, with the proviso that $R_6$ and $R_7$ cannot both be hydrogen; $X_3$ is selected from the group consisting of hydrogen, straight chain $C_1-C_8$ alkyl, and a moiety of the formula $C_qH_{2q}B$, wherein q is an integer 0 to 4 and b is selected from the group consisting of halophenyl, bishalophenyl and aminophenyl; the racemic mixture thereof; the mirror image thereof; and the non-toxic pharmaceutically acceptable salts thereof;

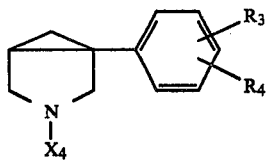

(IV)

wherein $R_3$ and $R_4$ are as defined above for Formula II with the proviso that $R_3$ and $R_4$ cannot both be hydrogen; $X_4$ is selected from the group consisting of $C_3$–$C_6$ cycloalkylmethyl, $C_3$–$C_6$ alkenyl and $C_3$–$C_6$ alkynyl; the racemic mixture thereof; the mirror image thereof; and the non-toxic pharmaceutically acceptable salts thereof;

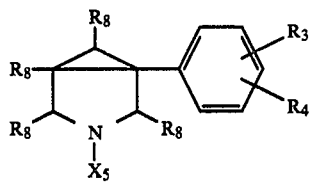

(V)

wherein $R_3$ and $R_4$ are as defined above for Formula II; $X_5$ is selected from the group consisting of hydrogen, straight chain $C_1$–$C_8$ alkyl, $C_3$–$C_6$ cycloalkylmethyl, $C_3$–$C_6$ alkenyl, $C_3$–$C_6$ alkynyl; and a moiety of the formula $C_rH_{2r}D$; wherein r is an integer 1 to 3 and D is selected from the group consisting of phenyl and p-fluorobenzoyl; $R_8$ is selected from the group consisting of hydrogen and $C_1$–$C_3$ alkyl; with the proviso that at least one $R_8$ must be selected from the group consisting of $C_1$–$C_3$ alkyl; the racemic mixture thereof; the mirror image thereof; and the non-toxic pharmaceutically acceptable salts thereof.

DETAILED DESCRIPTION OF THE INVENTION

The following terms, as used hereinabove and below, have the following meaning unless expressly stated to the contrary.

The term "$C_1$–$C_3$ alkyl" refers to a straight or branched chain, monovalent substituent consisting solely of carbon and hydrogen, containing no unsaturation, and having from 1 to 3 carbon atoms, e.g. methyl, ethyl, n-propyl, and isopropyl.

The term "$C_1$–$C_5$ alkyl" refers to a straight or branched chain, monovalent substituent consisting solely of carbon and hydrogen, containing no unsaturation, and having from 1 to 5 carbon atoms. Examples of such alkyl groups include those listed above for $C_1$–$C_3$ alkyl in addition to, e.g., n-butyl, t-butyl, n-pentyl, 2,2-dimethylpropyl, and the like.

The term "$C_1$–$C_6$ alkyl" refers to a straight or branched chain, monovalent substituent consisting solely of carbon and hydrogen, containing no unsaturation, and having from 1 to 6 carbon atoms. Examples of such alkyl groups include those listed above for $C_1$–$C_5$ alkyl in addition to, e.g., n-hexyl, 2-methylpentyl and the like.

The term "$C_1$–$D_8$ alkyl" refers to a straight or branched chain, monovalent substituent consisting solely of carbon and hydrogen, containing no unsaturation, and having from 1 to 8 carbon atoms. Examples of such alkyl groups include those listed above for $C_1$–$C_6$ alkyl in addition to, e.g., n-heptyl, 2,3,3-trimethylbutyl, 2,3-dimethylpentyl, 2-ethylpentyl, n-octyl, 3,5-dimethylhexyl, 2-isopropylpentyl, and the like.

The term "$C_1$–$C_6$ alkylamino" refers to an amino group in which one of the hydrogens has been replaced by one of the $C_1$–$C_6$ alkyl groups as defined above, having the free valence from the amino nitrogen, e.g., methylamino, ethylamino, n-propylamino, isopropylamino, t-butylamino, 2,3-dimethylbutylamino, and the like.

The term "di-$C_1$–$C_6$ alkylamino" refers to an amino group in which both hydrogens have been replaced by $C_1$–$C_6$ alkyl groups which may be the same or different and which are selected from those defined above, the free valence being on the amino nitrogen; e.g., dimethylamino, diethylamino, dipropylamino, ethylmethylamino, dipentylamino, and the like.

The term "$C_1$–$C_6$ alkoxy" refers to the above defined $C_1$–$C_6$ alkyl groups linked through an ether linkage, having the free valence from the ether oxygen, e.g. methoxyl, ethoxyl, n-propoxyl, isopropoxyl, butoxyl, sec-butoxyl, tert-butoxyl, pentyloxyl, hexyloxyl, and the like.

The term "$C_1$–$C_6$ alkoxymethyl" refers to a methyl group in which one of the hydrogens has been replaced by a $C_1$–$C_6$ alkoxy group as defined above, having the free valence from the methyl carbon, e.g. methoxymethyl, ethoxymethyl, n-propoxymethyl, t-butoxymethyl, and the like.

The term "$C_1$–$C_6$ alkanoyl" refers to the above defined $C_1$–$C_6$ alkyl groups having on the free valence carbon a ketone oxygen, e.g. formyl, acetyl, propionyl, butyryl, and the like.

The term "$C_3$–$C_6$ alkenyl" refers to a straight or branched chain, monovalent substituent consisting solely of carbon and hydrogen, containing one double bond, and having from 3 to 6 carbon atoms, e.g. allyl, 1-propenyl, 1-butenyl, 2-butenyl, 1-pentenyl, 2-pentenyl, 1-hexenyl, 3-hexenyl, and the like.

The term "$C_3$–$C_6$ alkynyl" refers to a straight or branched chain, monovalent substituent consisting solely of carbon and hydrogen, containing one triple bond, and having from 3 to 6 carbon atoms, e.g. 1-propynyl, 2-propynyl, 1-butynyl, 3-butynyl, and the like.

The term "halo" refers to fluoro, chloro, bromo, and iodo.

The term "halophenyl" refers to a phenyl group substituted with a fluoro, chloro, bromo, or iodo radical.

The term "$C_3$–$C_6$ cycloalkyl" refers to a three- to six-membered monovalent ring containing only hydrogen and carbon which is fully saturated, e.g. cyclopropyl, cyclobutyl, cyclopentyl, and cyclohexyl.

The term "$C_3$–$C_6$ cycloalkylmethyl" refers to the above disclosed $C_3$–$C_6$ cycloalkyl groups linked through a methyl group, having the free valence from the methyl carbon, e.g. cyclopropylmethyl, cyclobutylmethyl, cyclopentylmethyl, and cyclohexylmethyl.

The compounds of Formula I may be prepared as described below and as further illustrated by the accompanying Examples.

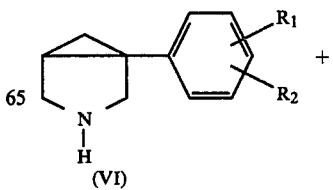

(VI)

-continued

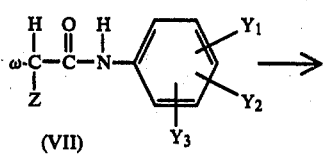

(VII)

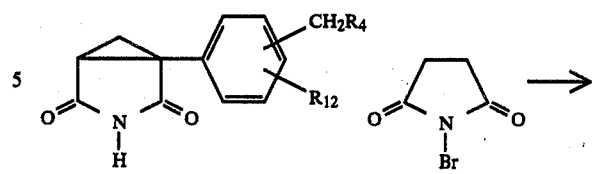

(XI)

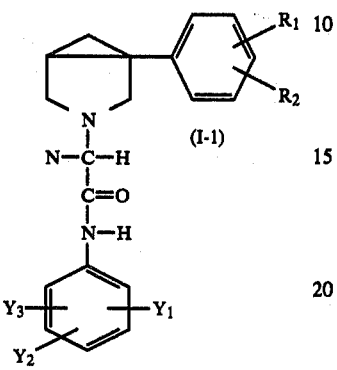

(I-1)

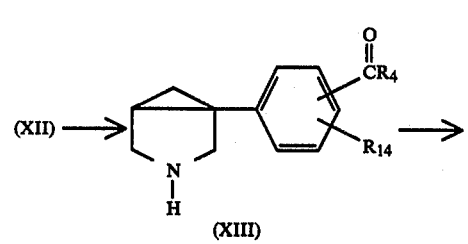

(XIII)

The compounds of Formula I-1 wherein $X_1$ is a radical of Formula IA as defined above and $R_1$ and $R_2$ are as defined above may be prepared from a compound of Formula VI wherein $R_1$ and $R_2$ are as defined above by the interaction with a compound of Formula VII wherein ω is a suitable leaving group such as bromine or chlorine; in a solvent such as benzene, toluene, or a $C_1$-$C_6$ alcohol, such as ethanol or n-butyl alcohol, in the presence of an acid scavenger such as sodium or potassium carbonate, at 25°-120° C. The starting materials of Formula VI wherein $R_1$ and $R_2$ are each independently selected from the group consisting of hydrogen and halogen are described in U.S. Pat. No. 4,131,611.

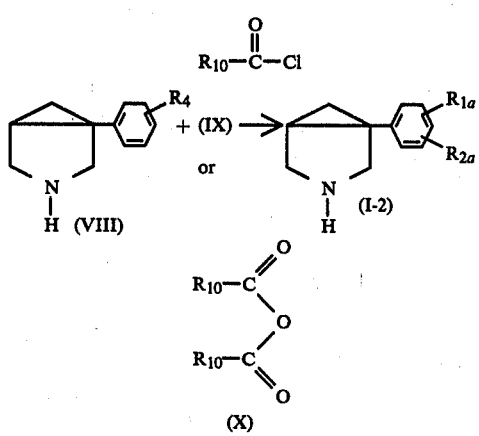

(X)

The compounds of Formula I-2 wherein $R_{1a}$ is $C_1$-$C_6$ alkanoyl or a radical of formula IB as defined above wherein p=1 and n is as previously defined, and $R_{2b}$ is hydrogen, halogen, $C_1$-$C_6$ alkylamino or di-$C_1$-$C_6$ alkylamino, may be prepared from a compound of Formula VIII wherein $R_9$ is hydrogen, halogen, $C_1$-$C_6$ alkylamino, or di-$C_1$-$C_6$ alkylamino by the interaction with an acid chloride of Formula IX or an acid anhydride of Formula X wherein $R_{10}$ is a $C_1$-$C_5$ alkyl or a radical of Formula IB as defined above wherein p=0, in the presence of a Lewis acid such as aluminum chloride or boron trifluoride, in an inert solvent such as dichloromethane or chlorobenzene at −10° C. to 20° C.

The compounds of Formula I-3 wherein $R_{1b}$ is a radical of Formula IC as defined above and $R_{2b}$ is hydrogen, halogen, or a radical of formula IC as defined above, may be prepared by reacting a compound of Formula XI wherein $R_{11}$ is hydrogen or $C_1$-$C_5$ alkyl and $R_{12}$ is hydrogen, halogen, or —$CH_2R_{11}$, with N-bromosuccinimide in the presence of a free-radical catalyst, such as benzoyl peroxide, in the presence of ultraviolet or visible light in an inert solvent such as carbon tetrachloride or chlorobenzene at 50°-120° C. to yield the corresponding dibromo derivatives of Formula XII, wherein $R_{11}$ is as defined above and $R_{13}$ is hydrogen, halogen, or —$CBr_2R_{11}$. The compound of Formula XII may then be hydrolyzed at 0°-80° C. with, e.g., water and a base such as potassium or calcium carbonate or sodium bicarbonate; or, e.g., with water and silver nitrate in the presence of a cosolvent such as acetone, to give a compound of Formula XIII wherein $R_{11}$ is as defined above and $R_{14}$ is hydrogen, halogen, or

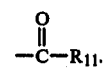

The compound of Formula XIII may be reduced at 0°-120° C. with a reducing agent such as lithium aluminum hydride or sodium bis(2-methoxyethoxy)aluminum hydride, in an inert solvent such as ethyl ether, tetrahydrofuran, or toluene, to yield a compound of Formula I-3 as defined above.

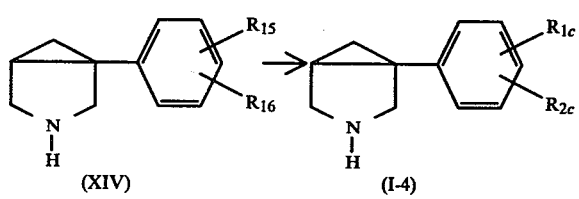

Compounds of Formula I-4 above wherein $R_{1c}$ is $C_1-C_6$ alkanoyl and $R_{2c}$ is hydrogen, halogen, or $C_1-C_6$ alkanoyl may be prepared from compounds of Formula XIV wherein $R_{15}$ is a radical of Formula IC as defined above and $R_{16}$ is hydrogen, halogen, or a radical of Formula IC as defined above, by oxidation according to the method of Corey and Schmidt, *Tetrahedron Letters*, 399(1979), using pyridinium dichromate in dichloromethane.

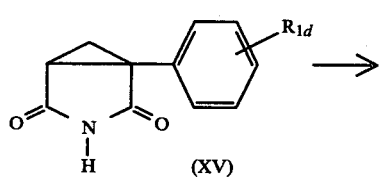

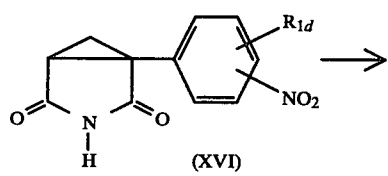

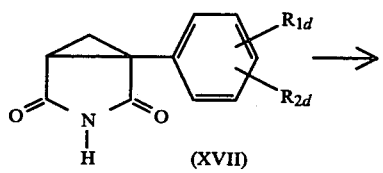

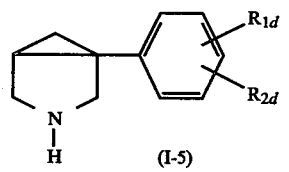

The compounds of Formula I-5 wherein $R_{1d}$ is hydrogen, halogen, $C_1-C_6$ alkylamino or di-$C_1-C_6$ alkylamino, and $R_{2d}$ is $C_1-C_6$ alkylamino or di-$C_1-C_6$ alkylamino may be prepared by reacting a compound of Formula XV wherein $R_{1d}$ is as defined above with a nitric acid, such as a fuming yellow nitric acid, at $-10°$ C. to $10°$ C. in a solvent such as dichloromethane or without a solvent, to yield the compound of Formula XVI wherein $R_{1d}$ is as defined above. The compound of formula XVI is then converted to the compound of Formula XVII, wherein $R_{1d}$ and $R_{2d}$ are as defined above, by reductive alkylation in the presence of a $C_1-C_6$ aldehyde or ketone such as formaldehyde, acetaldehyde, acetone, or 1-hexanal, in the presence of hydrogen and a reducing catalyst such as platinum oxide or paladium on charcoal (5–10% by weight), in a solvent such as methanol, ethanol or isopropyl alcohol, and in the presence of a weak acid such as acetic acid, in the temperature range $20°-80°$ C., and in the pressure range one to five atmospheres. The compound of Formula XVII is then reduced with a suitable reducing agent such as diborane, lithium aluminum hydride, or sodium bis(2-methoxyethoxy)aluminum hydride in an inert solvent such as tetrahydrofuran, ether, or toluene, in the temperature range $0°$ C. to $120°$ C.

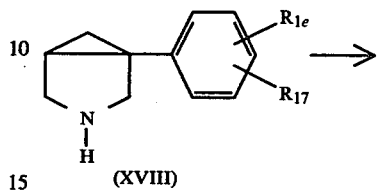

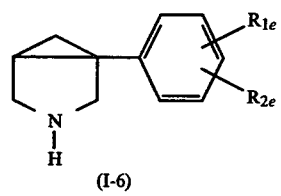

The compounds of Formula I-6 wherein $R_{1e}$ is hydrogen or halogen and $R_{2e}$ is a radical of the Formula IB wherein n is an integer 1 or 2, p is 0, and $Y_1$, $Y_2$, and $Y_3$ are as defined above, may be prepared from a compound of Formula XVIII wherein $R_{1e}$ is as defined above and $R_{17}$ is a radical of Formula IB wherein n=1, p=1, and $Y_1$, $Y_2$, and $Y_3$ are as defined above, by the procedure of the Clemmenson reduction using zinc metal and mercury(II)chloride in concentrated hydrochloric acid.

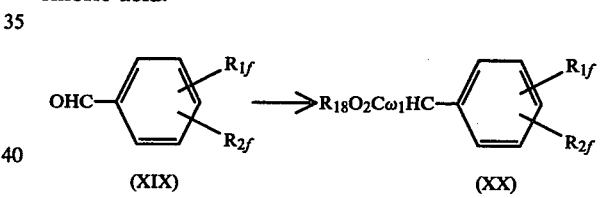

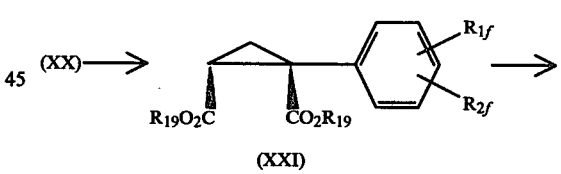

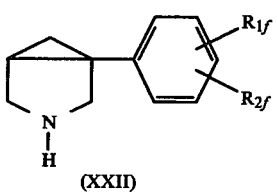

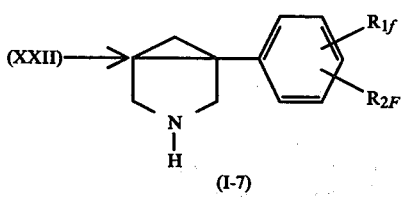

Compounds of Formula I-7, wherein $R_{1f}$ and $R_{2f}$ taken together are methylenedioxy may be prepared according to the following procedure.

Compounds of Formula XX wherein $R_{1f}$ and $R_{2f}$ are as defined above, $R_{18}$ is methyl or ethyl, and $\omega_1$ is bromine or chlorine, are prepared from the compound of Formula XIX wherein $R_{1f}$ and $R_{2f}$ are as defined above by formation of the cyanohydrin, followed by hydrolysis to the substituted mandelic acid, esterification with methanol or ethanol, and halogenation of the C-OH group with phosphorous tribromide or thionyl chloride, as described in Epstein, et al., J. Med. Chem. 24:481 (1981).

The compound of Formula XX is then reacted with methyl or ethyl acrylate in a solvent such as ether or toluene and in the presence of a strong base such as sodium hydride or sodium methoxide at 10°–55° C. to yield the corresponding diesters of Formula XXI wherein $R_{1f}$ and $R_{2f}$ are as defined above and $R_{19}$ is methyl or ethyl; the compound of Formula XXI is then converted to the corresponding compound of Formula XXI wherein $R_{19}$ is hydrogen by hydrolysis with a base such as potassium hydroxide in a solvent such as methanol or ethanol at a temperature of 50°–100° C.

The compounds of Formula XXI wherein $R_{1f}$ and $R_{2f}$ are as defined above and $R_{19}$ is hydrogen are then converted to compounds of Formula XXII wherein $R_{1f}$ and $R_{2f}$ are as defined above, by refluxing in a high boiling solvent such as toluene or xylene in the presence of urea or ammonia. Finally, the compound of Formula XXII is converted to the corresponding compound of Formula I-7 as defined above, by reduction with a reducing agent such as sodium bis(2-methoxyethoxy)aluminum hydride in benzene or toluene at 20°–120° C.

The present invention is also concerned with a method of treating depression and stress in warm-blooded animals using the novel compounds of Formula I as well as the known compounds of Formulas II–V. The term "depression" includes both reactive and endogenous depression. It is also anticipated that at least one of these compounds, 1-(p-tolyl)-3-azabicyclo[3.1.0-]hexane hydrochloride, will be useful in inducing mood elevation in depressed subjects.

The processes by which the compounds of Formulas II–V may be made are disclosed in U.S. Pat. No. 4,131,611 and are further illustrated by the examples of this specification.

The compounds of Formulas I–V may possess a chiral center. Accordingly, these compounds may be prepared in either their optically active form or as a racemic mixture. Unless otherwise specified, the compounds described herein are all in the racemic form. However, the scope of the subject invention is not to be considered limited to the racemic form, but to encompass the individual optical isomers of the compounds of Formulas I–V.

Where desired the individual diastereomeric and optically isomeric compounds can be isolated by conventional separation and purification procedures in the case of diastereomers and by conventional resolution procedures in the case of optical isomers. Optimum physical, or physical-chemical, separation procedures and resolution procedures can be obtained by routine trial and error procedures well within the scope of those skilled in the art.

The compounds of Formulas I–V may be in the acid-addition salt form. The term "pharmaceutically acceptable salts" refers to those acid-addition salts of the parent compound which do not significantly adversely affect the pharmaceutical properties (e.g., toxicity, effectiveness, etc.) of the parent compound such as are conventionally used in the pharmaceutical art. These acid-addition salts are prepared by treatment of the parent compound with the appropriate organic or inorganic acid in a manner well-known to those skilled in the art. The hydrochloride, phosphate, citrate, fumarate, maleate, succinate, pamoate, and sulfate acid-addition salts are preferred. Particularly preferred is the hydrochloride salt. It is to be understood that for the purposes of this invention, the acid-addition salts are equivalent to the parent free base.

The following compounds are preferred for use in the present invention:

(+)-1-(p-Chlorophenyl)-3-methyl-3-azabicyclo[3.1.0-]hexane hydrochloride 1-(p-Chlorophenyl)-3-methyl-3-azabicyclo[3.1.0]hexane hydrochloride 3-Ethyl-1-phenyl-3-azabicyclo[3.1.0]hexane hydrochloride 1-(3,4-Dichlorophenyl)-3-azabicyclo[3.1.0]hexane hydrochloride 1-(p-Tolyl)-3-azabicyclo[3.1.0]hexane hydrochloride 1-(m-hydroxyphenyl)-3-methyl-3-azabicyclo[3.1.0-]hexane hydrochloride Particularly preferred is 1-(p-tolyl)-3-azabicyclo[3.1.0]hexane hydrochloride.

The compounds of Formulas I–V are useful as anti-depressant agents in warm-blooded animals as verified in the following tests:

The anti-depressant properties of these compounds were tested by measuring their ability to counteract depression and ptosis induced by the administration of tetrabenazine hexamate at a dose of 30 mg. per kg. expressed as base. Each test compound was administered orally or intraperitoneally to 10 mice at a dose of 25 mg. per kg. of body weight 30 or 60 minutes prior to treatment with tetrabenazine. Thirty minutes later the mice were tested for their exploratory behavior as described by E. N. Greenblatt and A. C. Osterberg, Toxicology and Applied Pharmacology 7:566–578 (1965). A compound is considered active if 3 or more mice are protected against tetrabenazine-induced depression of exploratory behavior. The results of this test on representative compounds of this invention appear in Table I.

TABLE I

| Compound | Result |
|---|---|
| 1-(p-Chlorophenyl)-3-azabicyclo[3.1.0]hexane hydrochloride | Active |
| (+)-1-(p-Chlorophenyl)-3-azabicyclo[3.1.0]hexane hydrochloride | Active |
| (−)-1-(p-Chlorophenyl)-3-azabicyclo[3.1.0]hexane hydrochloride | Active |
| 1-Phenyl-3-azabicyclo[3.1.0]hexane hydrochloride | Active |
| 1-(m-Chlorophenyl)-3-azabicyclo[3.1.0]hexane hydrochloride | Active |
| 1-(m-Fluorophenyl)-3-azabicyclo[3.1.0]hexane hydrochloride | Active |
| 1-(p-Chlorophenyl)-3-methyl-3-azabicyclo[3.1.0]-hexane hydrochloride | Active |
| 1-[$\alpha,\alpha,\alpha$-trifluoro-(p-tolyl)]-3-azabicyclo-[3.1.0]hexane hydrochloride | Active |
| 1-(p-Methoxyphenyl)-3-azabicyclo[3.1.0]hexane hydrochloride | Active |
| (+)-1-Phenyl-3-azabicyclo[3.1.0]hexane hydrochloride | Active |
| (−)-1-Phenyl-3-azabicyclo[3.1.0]hexane hydrochloride | Active |
| 1-(m-Methoxyphenyl)-3-methyl-3-azabicyclo-[3.1.0]hexane hydrochloride | Active |
| 1-(3,4-Dichlorophenyl)-3-azabicyclo[3.1.0]-hexane hydrochloride | Active |
| 1-(p-Bromophenyl)-3-azabicyclo[3.1.0]hexane | Active |

TABLE I-continued

| Compound | Result |
|---|---|
| 1-[p-Chloro-α,α,α-trifluoro-m-tolyl]-3-azabicyclo[3.1.0]hexane hydrochloride | Active |
| 1-(p-Ethoxyphenyl)-3-azabicyclo[3.1.0]hexane hydrochloride | Active |
| 1-(3-Bromo-4-methoxyphenyl)-3-azabicyclo[3.1.0]hexane hydrochloride | Active |
| 1-(p-Tolyl)-3-azabicyclo[3.1.0]hexane hydrochloride | Active |
| 1-(p-Fluorophenyl)-3-azabicyclo[3.1.0]hexane hydrochloride | Active |
| 1-(3,4,5-Trimethoxyphenyl)-3-azabicyclo[3.1.0]hexane hydrochloride | Active |
| 1-(p-Aminophenyl)-3-azabicyclo[3.1.0]hexane dihydrochloride | Active |
| 1-(p-tert-Butylphenyl)-3-azabicyclo[3.1.0]hexane hydrochloride | Active |
| 3-Methyl-1-(p-tolyl)-3-azabicyclo[3.1.0]hexane hydrochloride | Active |
| 1-(p-Ethoxyphenyl)-3-azabicyclo[3.1.0]hexane hydrochloride | Active |
| 1-(p-Hexylphenyl)-3-azabicyclo[3.1.0]hexane hydrochloride | Active |
| 1-(m-Tolyl)-3-azabicyclo[3.1.0]hexane hydrochloride | Active |
| 1-(p-Isopropylphenyl)-3-azabicyclo[3.1.0]hexane hydrochloride | Active |
| 3-Cyclopropylmethyl-1-(p-tolyl)-3-azabicyclo[3.1.0]hexane hydrochloride | Active |
| 1-(m-Hydroxyphenyl)-3-methyl-3-azabicyclo[3.1.0]hexane hydrochloride | Active |
| 1-(4-Biphenyl)-3-azabicyclo[3.1.0]hexane hydrochloride | Active |
| 4-Methyl-1-(p-tolyl-3-azabicyclo[3.1.0]hexane hydrochloride | Active |
| 3,4-Dimethyl-1-(p-tolyl)-3-azabicyclo[3.1.0]hexane hydrochloride | Active |
| 4'-(3-Azabicyclo[3.1.0]hex-1-yl)acetophenone hydrochloride | Active |
| 1-(3,4-Methylenedioxyphenyl)-3-azabicyclo[3.1.0]hexane hydrochloride | Active |
| 4-Ethyl-1-(p-tolyl)-3-azabicyclo[3.1.0]hexane hydrochloride | Active |
| 4'-(3-Azabicyclo[3.1.0]hex-1-yl)benzophenone hydrochloride | Active |
| 4'-(3-Azabicyclo[3.1.0]hex-1-yl)propiophenone hydrochloride | Active |
| 1-[α-Phenyl-(p-tolyl]-3-azabicyclo[3.1.0]hexane hydrochloride | Active |
| 1-(p-Isopropoxyphenyl)-3-azabicyclo[3.1.0]hexane hydrochloride | Active |
| p-(3-Azabicyclo[3.1.0]hex-1-yl)benzyl alcohol | Active |
| 1-(p-Diethylaminophenyl)-3-azabicyclo[3.1.0]hexane dihydrochloride | Active |
| 1-(3,4-Dimethylphenyl)-3-azabicyclo[3.1.0]hexane hydrochloride | Active |
| 3-Benzyl-1-phenyl-3-azabicyclo[3.1.0]hexane hydrochloride | Active |
| 3-Phenethyl-1-phenyl-3-azabicyclo[3.1.0.]hexane hydrochloride | Active |
| 3-Ethyl-1-(p-chlorophenyl)-3-azabicyclo[3.1.0]hexane | Active |
| 3-Isopropyl-1-phenyl-3-azabicyclo[3.1.0]hexane hydrochloride | Active |
| 3-(p-Chlorobenzyl)-1-(p-chlorophenyl)-3-azabicyclo[3.1.0]hexane | Active |
| 3-(1-Adamantylmethyl)-1-(p-chlorophenyl)-3-azabicyclo[3.1.0]hexane | Active |
| 3-Allyl-1-phenyl-3-azabicyclo[3.1.0]hexane hydrochloride | Active |
| 3-Ethyl-1-phenyl-3-azabicyclo[3.1.0]hexane hydrochloride | Active |
| 3-Cyclohexylmethyl-1-phenyl-3-azabicyclo[3.1.0]hexane hydrochloride | Active |
| 3-(m-Fluorobenzyl)-1-(p-chlorophenyl)-3-azabicyclo[3.1.0]hexane hydrochloride | Active |
| 3-(5-Norbornen-2-yl-methyl)-1-(p-chlorophenyl)-3-azabicyclo[3.1.0]hexane hydrochloride | Active |
| 3-(2-Napthylmethyl)-1-(p-chlorophenyl)-3-azabicyclo[3.1.0]hexane hydrochloride | Active |
| 3-Ethyl-1-(p-tolyl)-3-azabicyclo[3.1.0]hexane hydrochloride | Active |
| (−)-3-Methyl-1-phenyl-3-azabicyclo[3.1.0]hexane hydrochloride | Active |
| 1-(p-Ethylaminoiphenyl)-3-azabicyclo[3.1.0]hexane dihydrochloride | Active |
| 1-(p-Trifluoromethylphenyl)-3-azabicyclo[3.1.0]hexane hydrochloride | Active |
| (+)-3-Methyl-1-(p-chlorophenyl)-3-azabicyclo[3.1.0]hexane hydrochloride | Active |
| 3-Allyl-1-(p-tolyl)-3-azabicyclo[3.1.0]hexane hydrochloride | Active |
| 1-(3,4-Dichlorophenyl)-3-methyl-3-azabicyclo[3.1.0]hexane hydrochloride | Active |

Effects on tetrabenazine-induced ptosis was observed concomitantly with exploratory behavior. A compound is considered active if 6 or more mice exhibit ≧75% opening of the palpebral aperture (eyelid). The results of this test on representative compounds of Formulas I–V appear in Table II.

TABLE II

| Compound | Result |
|---|---|
| 1-(p-Chlorophenyl)-3-azabicyclo[3.1.0]hexane hydrochloride | Active |
| (+)-1-(p-Chlorophenyl)-3-azabicyclo[3.1.0]hexane hydrochloride | Active |
| (−)-1-(p-Chlorophenyl)-3-azabicyclo[3.1.0]hexane hydrochloride | Active |
| 1-Phenyl-3-azabicyclo[3.1.0]hexane hydrochloride | Active |
| 1-(m-Chlorophenyl)-3-azabicyclo[3.1.0]hexane hydrochloride | Active |
| 1-(m-Fluorophenyl)-3-azabicyclo[3.1.0]hexane hydrochloride | Active |
| 1-(p-Chlorophenyl)-3-methyl-3-azabicyclo[3.1.0]hexane hydrochloride | Active |
| 1-[α,α,α-Trifluoro-(p-tolyl)]-3-azabicyclo[3.1.0]hexane hydrochloride | Active |
| 1-(p-Methoxyphenyl)-3-azabicyclo[3.1.0]hexane hydrochloride | Active |
| (+)-1-Phenyl-3-azabicyclo[3.1.0]hexane hydrochloride | Active |
| (−)-1-Phenyl-3-azabicyclo[3.1.0]hexane hydrochloride | Active |
| 1-(m-Methoxyphenyl)-3-methyl-3-azabicyclo[3.1.0]hexane hydrochloride | Active |
| 1-(3,4-Dichlorophenyl)-3-azabicyclo[3.1.0]hexane hydrochloride | Active |
| 1-(p-Bromophenyl)-3-azabicyclo[3.1.0]hexane hydrochloride | Active |
| 1-[α,α,α-Trifluoro-(m-tolyl)]-3-azabicyclo[3.1.0]hexane hydrochloride | Active |
| 1-(p-Chloro-α,α,α-trifluoro-m-tolyl)-3-azabicyclo[3.1.0]hexane hydrochloride | Active |
| 1-(p-Ethoxyphenyl)-3-azabicyclo[3.1.0]hexane hydrochloride | Active |
| 1-(3-Bromo-4-methoxyphenyl)-3-azabicyclo[3.1.0]hexane hydrochloride | Active |
| 1-(p-Tolyl)-3-azabicyclo[3.1.0]hexane hydrochloride | Active |
| 1-(p-Fluorophenyl)-3-azabicyclo[3.1.0]hexane hydrochloride | Active |
| 1-(3,4,5-Trimethoxyphenyl)-3-azabicyclo[3.1.0]hexane hydrochloride | Active |
| 1-(p-Aminophenyl)-3-azabicyclo[3.1.0]hexane dihydrochloride | Active |
| 1-(p-tert-Butylphenyl)-3-azabicyclo[3.1.0]hexane hydrochloride | Active |
| 3-Methyl-1-(p-tolyl)-3-azabicyclo[3.1.0]hexane hydrochloride | Active |
| 1-(p-Ethylphenyl)-3-azabicyclo[3.1.0]hexane hydrochloride | Active |
| 1-(m-Tolyl)-3-azabicyclo[3.1.0]hexane hydrochloride | Active |
| (+)-1-(p-Tolyl)-3-azabicyclo[3.1.0]hexane hydrochloride | Active |
| 1-(p-Isopropylphenyl)-3-azabicyclo[3.1.0]hexane hydrochloride | Active |

TABLE II-continued

| Compound | Result |
|---|---|
| 3-Cyclopropylmethyl-1-(p-tolyl)-3-azabicyclo-[3.1.0]hexane hydrochloride | Active |
| 1-(m-Hydroxyphenyl)-3-methyl-3-azabicyclo-[3.1.0]hexane hydrochloride | Active |
| 1-(4-Biphenyl)-3-azabicyclo[3.1.0]hexane hydrochloride | Active |
| 4-Methyl-1-(p-tolyl)-3-azabicyclo[3.1.0]hexane hydrochloride | Active |
| 4'-(3-Azabicyclo[3.1.0]hex-1-yl)acetophenone hydrochloride | Active |
| 1-(3,4-Methylenedioxyphenyl)-3-azabicyclo-[3.1.0]hexane hydrochloride | Active |
| 4-Ethyl-1-(p-tolyl)-3-azabicyclo[3.1.0]hexane hydrochloride | Active |
| 4'-(3-Azabicyclo[3.1.0]hex-1-yl)benzophenone hydrochloride | Active |
| 4'-(3-Azabicyclo[3.1.0]hex-1-yl)propiophenone hydrochloride | Active |
| 1-[α-Phenyl-(p-tolyl)]-3-azabicyclo[3.1.0]hexane hydrochloride | Active |
| 1-(p-Isopropoxyphenyl)-3-azabicyclo[3.1.0]-hexane hydrochloride | Active |
| p-(3-Azabicyclo[3.1.0]hex-1-yl)benzyl alcohol | Active |
| 1-(p-Diethylaminophenyl)-3-azabicyclo[3.1.0]-hexane dihydrochloride | Active |
| 1-(3,4-Dimethylphenyl)-3-azabicyclo[3.1.0]-hexane hydrochloride | Active |
| 3-Benzyl-1-phenyl-3-azabicyclo[3.1.0]hexane hydrochloride | Active |
| 3-Cyclopropylmethyl-1-phenyl-3-azabicyclo[3.1.0]-hexane hydrochloride | Active |
| 3-Phenethyl-1-phenyl-3-azabicyclo[3.1.0]hexane hydrochloride | Active |
| 3-Ethyl-1-(p-chlorophenyl)-3-azabicyclo[3.1.0]-hexane | Active |
| 3-Isopropyl-1-phenyl-3-azabicyclo[3.1.0]hexane hydrochloride | Active |
| 3-(p-Chlorobenzyl)-1-(p-chlorophenyl)-3-aza-bicyclo[3.1.0]hexane | Active |
| 3-(1-Adamantylmethyl)-1-(p-chlorophenyl)-3-azabicyclo[3.1.0]hexane | Active |
| 3-Allyl-1-phenyl-3-azabicyclo[3.1.0] hexane hydrochloride | Active |
| 3-Ethyl-1-phenyl-3-azabicyclo[3.1.0]hexane hydrochloride | Active |
| 3-Cyclohexylmethyl-1-phenyl-3-azabicyclo[3.1.0]-hexane hydrochloride | Active |
| 3-m-Fluorobenzyl)-1-(p-chlorophenyl)-3-azabicy-clo[3.1.0]hexane hydrochloride | Active |
| 3-(5-Norbornen-2-ylmethyl)-1-(p-chlorophenyl)-3-azabicyclo[3.1.0]hexane hydrochloride | Active |
| 3-(2-Naphthylmethyl)-1-(p-chlorophenyl)-3-azabicyclo[3.1.0]hexane hydrochloride | Active |
| 1-(m-Chlorophenyl)-3-methyl-3-azabicyclo-[3.1.0]hexane hydrochloride | Active |
| 3-Ethyl-1-(p-tolyl)-3-azabicyclo[3.1.0]hexane hydrochloride | Active |
| (−)-3-Methyl-1-phenyl-3-azabicyclo[3.1.0]hexane hydrochloride | Active |
| (+)-1-(p-Chlorophenyl)-3-methyl-3-azabicyclo-[3.1.0]hexane hydrochloride | Active |
| 1-(m-Methoxyphenyl)-3-azabicyclo[3.1.0]hexane hydrochloride | Active |
| 1-(3,4-Dichlorophenyl)-3-methyl-3-azabicyclo-[3.1.0]hexane hydrochloride | Active |
| 1-(p-Trifluoromethylphenyl)-3-azabicyclo-[3.1.0]hexane hydrochloride | Active |

The compounds of Formulas I–V are active as antistress agents in warm-blooded animals as evidenced by their results when tested in the Stress Induced Depressed Behavior Test.

In this test, rats are confined on a warm (44.5° C.) but aversive surface for 15 minutes. After about 5–6 minutes, control rats begin to show episodes of depressed ("coping") behavior where they remain flat and immobile for short to long periods of time. The onset and total duration of this behavior is timed. A ratio of onset/duration is calculated. The test compounds are administered intraperitoneally at 10–20 mg. per kg. of body weight. Active compounds prolong the time of onset and shorten the duration time resulting in high ratios. The criterion for efficacy is a ratio $\geq 3.2$. The results for typical compounds of this invention appear in Table III.

TABLE III

| Compound | Result |
|---|---|
| 1-(p-Chlorophenyl)-3-azabicyclo[3.1.0]-hexane hydrochloride | Active |
| (+)-1-(p-Chlorophenyl)-3-azabicyclo[3.1.0]-hexane hydrochloride | Active |
| 1-Phenyl-3-azabicyclo[3.1.0]hexane hydrochloride | Active |
| (−)-1-Phenyl-3-azabicyclo[3.1.0]hexane hydrochloride | Active |
| 1-(p-Methoxyphenyl)-3-azabicyclo[3.1.0]-hexane hydrochloride | Active |
| (+)-1-Phenyl-3-azabicyclo[3.1.0]hexane hydrochloride | Active |
| 1-(m-Methoxyphenyl)-3-methyl-3-azabicyclo-[3.1.0]hexane hydrochloride | Active |
| 1-(3,4-Dichlorophenyl)-3-azabicyclo[3.1.0]-hexane hydrochloride | Active |
| 1-(p-Cyclohexylphenyl)-3-azabicyclo[3.1.0]-hexane | Active |
| 1-(p-Tolyl)-3-azabicyclo[3.1.0]hexane hydrochloride | Active |
| 1-(p-Aminophenyl)-3-azabicyclo[3.1.0]hexane dihydrochloride | Active |
| 3-Methyl-1-p-tolyl-3-azabicyclo[3.1.0]hexane hydrochloride | Active |
| (+)-1-(p-Tolyl)-3-azabicyclo[3.1.0]hexane hydrochloride | Active |
| (−)-1-(p-Tolyl)-3-azabicyclo[3.1.0]hexane hydrochloride | Active |
| 1-[(3,4-Methylenedioxy)phenyl]-3-azabicyclo-[3.1.0]hexane hydrochloride | Active |
| p-(3-Azabicyclo[3.1.0]hex-1-yl)benzyl alcohol | Active |
| 1-(3,4-Dimethylphenyl0-3-azabicyclo[3.1.0]-hexane hydrochloride | Active |
| 3-Ethyl-1-phenyl-3-azabicyclo[3.1.0]hexane hydrochloride | Active |

The active compounds of Formulas I–V are effective anti-depressant and antistress agents in warm-blooded animals when administered in amounts ranging from about 5 mg. to about 30 mg. per kg. of body weight per day. A preferred dosage regimen for optimum results would be from about 5 mg. to about 20 mg. per kg. of body weight per day, and such dosage units are employed so that a total of from about 350 mg. to about 1.5 g. of the active compound for a subject of about 70 kg. of body weight are administered in a 24 hour period. This dosage regimen may be adjusted to provide the optimum therapeutic response. For example, several divided doses may be administered daily, or the dose may be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent may be added such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts used. In addition, these active compounds may be incorporated into sustained-release preparations and formulations.

These active compounds may also be administered parenterally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The following Examples describe preparation of representative compounds of Formulas I–V and representative compositions containing said compounds. As used hereinabove and below unless expressly stated to the contrary, all temperature and temperature ranges refer to the centigrade system and the terms ambient or room temperature refer to about 20° C. The term percent or (%) refers to weight percent and the terms mole and moles refer to gram moles. The term equivalent refers to a quantity of reagent equal in moles to the moles of the preceding or succeeding reactant cited in the Preparation or Example in the terms of moles of finite weight or volume. As noted earlier, compounds having asymmetric centers and optical activity were isolated in their racemic form (±) unless otherwise indicated. References to "J. Med. Chem. 24:481" refer to J. W. Epstein et al., "1-Aryl-3-azabicyclo[3.1.0]hexanes, a New Series of Nonnarcotic Analgesic Agents", J. Med. Chem. 24:481 (1981).

EXAMPLE 1

1-(p-Chlorophenyl)-3-azabicyclo[3.1.0]hexane hydrochloride

A solution of 2 g. of diethyl 1-(p-chlorophenyl)-cis-1,2-cyclopropanedicarboxylate (U.S. Pat. No. 3,344,026, Ex. 1) in 25 ml. of ethanol is treated with 13.5 ml. of 1 N potassium hydroxide solution. The reaction mixture is refluxed for 3.5 hours and then is allowed to stand at room temperature overnight. The ethanol is removed under reduced pressure and the aqueous solution is extracted with ether to remove a small amount of mineral oil. The aqueous solution is treated with 13.5 ml. of 1 N hydrochloric acid and 2 ml. of 6 N hydrochloric acid. The oily aqueous mixture is extracted four times with chloroform. The chloroform solution is dried, decolorized, and concentrated under reduced pressure to give a yellow solid. Two recrystallizations from ethyl acetate-petroleum ether (30°–70° C.) give 0.85 g. of a white solid, 1-(p-chlorophenyl)-cis-1,2-cyclopropanedicarboxylic acid.

A 5.7 g. portion of the above acid and 2.02 g. of urea in 200 ml. of xylene is refluxed for 22 hours, cooled, diluted with benzene and washed with water. The organic layer is diluted with chloroform, dried, concentrated under reduced pressure and recrystallized from ethyl acetate and petroleum ether to give 1-(p-chlorophenyl)-1,2-cyclopropanedicarboximide.

To a stirred solution of 30 ml. of Vitride ® [sodium bis(2-methoxyethoxy)aluminum hydride (70% benzene solution)] is added dropwise a solution of 2.2 g. of 1-(p-chlorophenyl)-1,2-cyclopropanedicarboximide in 100 ml. of benzene over a 30 minute period at room temperature under nitrogen atmosphere. The reaction vessel is warmed slightly to maintain solution. The clear yellow solution is then heated to reflux under a nitrogen atmosphere for one hour. The solution is cooled and the excess reagent decomposed with 5 N sodium hydroxide. Water is added to the mixture and the benzene phase is separated. The aqueous phase is extracted with ether and the ether extracts are combined with the benzene phase and dried over magnesium sulfate. This organic phase is evaporated under reduced pressure to give a viscous liquid, which crystallizes to a tacky off-white solid consisting of the racemic base 1-(p-chlorophenyl)-3-azabicyclo[3.1.0]hexane. This solid is dissolved in ethanol, acidified with ethanolic hydrogen chloride, and ether is added producing off-white crystals of the hydrochloride. This is recrystallized from ethanol giving off-white crystals, m.p. 215°–217° C.

In a like manner, reductions of the following imides with Vitride ® yield the corresponding reduced products.

| Imide | Reduction Product |
|---|---|
| 1-phenyl-2-methyl-1,2,-cyclopropanedicarboximide (U.S. Pat. No. 3,166,571-Example 15) | 1-phenyl-5-methyl-3-azabicyclo[3.1.0]hexane hydrochloride, m.p. 161–163° C. |
| N—methyl-1-(3,4,5-tri- | 3-methyl-1-(3,4,5-trimeth- |

| Imide | Reduction Product |
|---|---|
| methoxyphenyl)-1,2-cyclo-propanedicarboximide (U.S. Pat. No. 3,166,571-Example 4) | oxyphenyl)-3-azabicyclo-[3.1.0]hexane hydrochloride, m.p. 243–245° C. |
| 1-(p-tolyl)-3,N—dimethyl-1,2-cyclopropanedicarbox-imide (U.S. Pat. No. 3,166,571-Example 11) | 1-(p-tolyl)-3,6-dimethyl-3-azabicyclo[3.1.0]hexane |

EXAMPLE 2

(+)-1-(p-chlorophenyl)-3-azabicyclo[3.1.0]hexane hydrochloride

A 192.5 g. portion of racemic cis-1-(p-chlorophenyl)-1,2-cyclopropanedicarboxylic acid (U.S. Pat. No. 3,892,772) and 142 g. of (−)-2-aminobutanol in 1600 ml. of acetone is allowed to stand for 48 hours, filtered and washed with acetone giving a solid. This solid is dissolved in 460 ml. of warm water and acidified. The solid is filtered and air dried. A 107.5 g. portion of this crude (+)-diacid and 79.3 g. of (−)-2-aminobutanol in 892 ml. of acetone are allowed to stand several hours. The solid is filtered, dried, dissolved in 200 ml. of warm water, acidified with concentrated hydrochloric acid, cooled and filtered. This solid is recrystallized from acetonitrile giving (+)-cis-1-(p-chlorophenyl)-1,2-cyclopropanedicarboxylic acid, $[\alpha]_D^{CH3OH} = +180°$.

A 10.5 g. portion of this (+)-diacid and 3.9 g. of urea in 325 ml. of xylene is stirred, then refluxed for 7.5 hours and allowed to stand overnight. Distilling off the xylene, cooling and filtration produces a white solid which is recrystallized from ethanol giving (+)-1-(p-chlorophenyl)-1,2-cyclopropanedicarboximide $[\alpha]_D^{CH3OH} = +63°$.

To a stirred solution of 30 ml. of Vitride® (70% benzene solution) is added dropwise a solution of 4.5 g. of (+)-1-(p-chlorophenyl)-1,2-cyclopropanedicarboximide in 400 ml. of benzene during a 45 minute period with stirring at room temperature under nitrogen. The clear yellow solution is heated at reflux under nitrogen for 90 minutes and stored overnight at room temperature. The excess hydride reagent is decomposed by the cautious addition of 25 ml. of 5 N sodium hydroxide. The mixture is diluted with 200 ml. of water and the benzene phase is removed. The aqueous phase is extracted with chloroform. The combined benzene and chloroform phases are dried over magnesium sulfate and concentrated under reduced pressure to give (+)-1-(p-chlorophenyl)-3-azabicyclo[3.1.0]hexane as a tacky yellow solid. This solid is dissolved in ethanol and acidified with 20 ml. of 2.3 N ethanolic hydrogen chloride. A 200 ml. volume of ether is added and crystals form. These are recrystallized from acetonitrile to give the hydrochloride as white crystals, m.p. 190°–192° C.; $[\alpha]_D^{CH3OH} = +63°$.

EXAMPLE 3

1-Phenyl-3-azabicyclo[3.1.0]hexane hydrochloride

To a stirred solution of 30 ml. of Vitride® (70% benzene solution) is added dropwise a solution of 6.6 g. of 1-phenyl-1,2-cyclopropanedicarboximide (U.S. Pat. No. 3,166,571, Ex. 8) in 400 ml. of benzene, during one hour at room temperature under nitrogen. The reaction mixture is then heated at reflux under nitrogen for 90 minutes. The excess hydride reagent is decomposed by the cautious addition of 25 ml. of 10 N sodium hydroxide. The mixture is diluted with 200 ml. of water and the benzene phase is separated. The aqueous phase is extracted with chloroform and the combined organic extracts are dried over magnesium sulfate. The solution is concentrated under reduced pressure to give a brown liquid which is dissolved in ethanol and acidified with 5 ml. of 2.3 N ethanolic hydrogen chloride. The addition of ether precipitates a solid which is recrystallized from acetonitrile to give white crystals, m.p. 166°–168° C.

EXAMPLE 4

3-Methyl-1-phenyl-3-azabicyclo[3.1.0]hexane hydrochloride

To a stirred solution of 30 ml. of Vitride® (70% benzene solution) is added dropwise a solution of 5.5 g. of N-methyl-1-phenyl-1,2-cyclopropanedicarboximide (U.S. Pat. No. 3,166,571, Ex. 1) in 400 ml. of benzene over a one hour period at room temperature under nitrogen. The mixture is heated at reflux under nitrogen for 90 minutes. The excess hydride reagent is decomposed by the cautious addition of 25 ml. of 10 N sodium hydroxide and then diluted to 200 ml. with water. The benzene phase is separated and the aqueous phase is extracted with chloroform. The combined organic phases are dried over magnesium sulfate and concentrated under reduced pressure giving a liquid. The liquid is dissolved in ethanol and acidified with 15 ml. of 2.3 N ethanolic hydrogen chloride. The addition of ether causes the formation of a solid which is recrystallized from isopropyl alcohol-hexane giving white crystals, m.p. 158°–160° C.

EXAMPLE 5

1-(m-Chlorophenyl)-3-azabicyclo[3.1.0]hexane hydrochloride

A 53.6 g. portion of ethyl m-chlorophenylacetate (prepared by esterification of the corresponding acid), 51.5 g. of N-bromosuccinimide and one gram of benzoyl peroxide in 1.25 liters of carbon tetrachloride is stirred with a Nichrome metal stirrer and refluxed for 20 hours. The mixture is cooled, filtered and concentrated to an orange oil. Vacuum distillation yields the product ethyl α-bromo-m-chlorophenylacetate.

To a stirred suspension of 4.4 g. of sodium hydride in 500 ml. of ether under nitrogen is added 0.5 ml. of ethanol. A mixture of 27.8 g. of the above ester, 10 g. of ethyl acrylate and one ml. of ethanol is added dropwise and the mixture is stirred at room temperature overnight. Ethanol is added to decompose the unreacted sodium hydride and the mixture is washed with 100 ml. of water. The product is dried and concentrated under reduced pressure to a yellow liquid, 1-(m-chlorophenyl)-1,2-cyclopropanedicarboxylic acid diethyl ester.

A 22 g. portion of this diester in 150 ml. of ethanol and 150 ml. of 1 N potassium hydroxide is refluxed for 3.5 hours and then allowed to stand at room temperature overnight. The mixture is concentrated and extracted with ether. The aqueous phase is acidified with 1 N hydrochloric acid, extracted three times with chloroform, dried and concentrated under reduced pressure to a yellow oil which is crystallized from ethyl acetate-petroleum ether to give cis-1-(m-chlorophenyl)-1,2-cyclopropanedicarboxylic acid as a white solid.

A 5.7 g. portion of this acid and 2.02 g. of urea in 200 ml. of xylene is refluxed for 22 hours, cooled, diluted with benzene and washed with water. The organic layer is diluted with chloroform, dried, concentrated under reduced pressure, and recrystallized from ethyl acetate and petroleum ether to give 1-(m-chlorophenyl)-1,2-cyclopropanedicarboximide.

To a stirred solution of 30 ml. of Vitride ® (70% benzene solution) is added dropwise a solution of 4.0 g. of 1-(m-chlorophenyl)-1,2-cyclopropanedicarboximide in 400 ml. of benzene during one hour at room temperature under nitrogen. The reaction is heated at reflux under nitrogen for 90 minutes. The excess hydride reagent is decomposed with 25 ml. of 10 N sodium hydroxide and the mixture is diluted with 200 ml. of water. The benzene phase is removed and the aqueous phase is extracted with chloroform. The combined organic phase are dried over magnesium sulfate and concentrated under reduced pressure to give a viscous orange-brown liquid. This liquid is dissolved in ethanol and acidified with 2.3 N ethanolic hydrogen chloride. The addition of ether precipitates a solid which is recrystallized from isopropanol to give 1-(m-chlorophenyl)-3-azabicyclo[3.1.0]hexane hydrochloride as white crystals, m.p. 182°–184° C.

EXAMPLE 6

1-(m-Fluorophenyl)-3-azabicyclo[3.1.0]hexane hydrochloride

A 46.2 g. portion of 1-(m-fluorophenyl)acetic acid is dissolved in 120 ml. of ethanol. A 12 ml. portion of sulfuric acid is added, the mixture is refluxed for 4.5 hours and then allowed to stand at room temperature overnight. A 400 ml. portion of water is added and the mixture is extracted three times with ether, dried over magnesium sulfate and concentrated under reduced pressure to a liquid. Vacuum distillation produces ethyl 1-(m-fluorophenyl)acetate.

A mixture of 49.3 g. of ethyl 1-(m-fluorophenyl)acetate, 53 g. of N-bromosuccinimide and 0.95 g. of benzoyl peroxide in 1.6 liters of carbon tetrachloride is refluxed and stirred with a Nichrome metal stirrer for 24 hours, concentrated to an orange oil and vacuum distilled giving ethyl α-bromo-1-(m-fluorophenyl)acetate.

To a suspension of 11 g. of sodium hydride in mineral oil in one liter of ether under nitrogen is added dropwise, with stirring, a mixture of 65 g. of ethyl α-bromo-1-(m-fluorophenyl)acetate, 25 g. of ethyl acrylate and 2 ml. of ethanol. The temperature is maintained at 25°–29° C. with stirring overnight. The mixture is cooled, a few ml. of ethanol are added to decompose the unreacted sodium hydride and the mixture is washed successively with water, 1 N hydrochloric acid, dilute sodium bicarbonate and saturated sodium chloride solution, then concentrated to a liquid which is vacuum distilled giving the diethyl ester of 1-(m-fluorophenyl)-1,2-cyclopropanedicarboxylic acid.

A mixture of 20.5 g. of the above diester and 160 ml. of 1 N potassium hydroxide in 150 ml. of ethanol is refluxed for 3.5 hours and concentrated. The mixture is acidified with 1 N hydrochloric acid, extracted three times with chloroform, dried and concentrated under reduced pressure to a solid. The solid is recrystallized twice from ethyl acetate-petroleum ether giving cis-1-(m-fluorophenyl)-1,2-cyclopropanedicarboxylic acid.

A stirred mixture of 8.0 g. of the above diacid and 2.6 g. of urea in 500 ml. of xylene is heated under reflux for 22 hours. The solution is diluted with benzene, washed with water and dried over magnesium sulfate. The organic layer is concentrated under reduced pressure to give 1-(m-fluorophenyl)-1,2-cyclopropanedicarboximide as and off-white solid.

To a stirred solution of 30 ml. of Vitride ® is added dropwise a solution of 5.6 g. of 1-(m-fluorophenyl)-1,2-cyclopropanedicarboximide in 400 ml. of benzene during 90 minutes, under nitrogen at room temperature. The reaction mixture is heated at reflux, under nitrogen for 90 minutes. The excess hydride reagent is decomposed by the cautious addition of 25 ml. of 10 N sodium hydroxide and then the mixture is diluted with 200 ml. of water. The benzene phase is removed and the aqueous phase is extracted with chloroform. The combined organic solutions are dried over magnesium sulfate and concentrated under reduced pressure to give a mixture of an oily solid and a viscous liquid. This mixture is dissolved in ethanol and acidified with ethanolic hydrogen chloride. The addition of ether gives a precipitate which is recrystallized from acetonitrile to give 1-(m-fluorophenyl)-3-azabicyclo[3.1.0]hexane hydrochloride as gray crystals, m.p. 140°–146° C.

EXAMPLE 6A (−)-1-Phenyl-3-azabicyclo[3.1.0]hexane hydrochloride

To a stirred slurry of 18.7 g. of (−)-1-phenyl-1,2-cyclopropanedicarboximide (U.S. Pat. No. 4,131,611, Ex. 8) in 500 ml. of benzene under nitrogen is added 150 ml. of Vitride ® over a period of 10 minutes. The mixture is stirred at room temperature for 2 hours, refluxed for 4 hours and then allowed to stand at room temperature for 20 hours. A 150 ml. portion of 10 N sodium hydroxide is added cautiously with stirring. The organic layer is washed with water, dried over magnesium sulfate and evaporated under reduced pressure to a yellow oil. This oil is dissolved in 300 ml. of ether. Dry hydrogen chloride gas is bubbled through until precipitation ceases and the mixture is filtered giving colorless crystals. These are recrystallized from acetonitrile giving pale tan crystals, m.p. 170°–172° C.

EXAMPLE 7

1-Phenyl-3-azabicyclo[3.1.0]hexane

To a stirred slurry of 18.7 g. of 1-phenyl-1,2-cyclopropanedicarboximide (U.S. Pat. No. 3,166,571, Ex. 8) in 500 ml. of benzene under nitrogen, is added 150 ml. of Vitride ® (70% benzene solution) over a period of 10 minutes. The mixture is stirred for 2 hours, refluxed for 4 hours and then allowed to stand for 20 hours. A 150 ml. portion of 10 N sodium hydroxide is added cautiously with stirring. The organic layer is washed with water, dried over magnesium sulfate and evaporated under reduced pressure to give the desired product as an oil, b.p. 130°–133° C./15 mm.

EXAMPLE 8

(+)-1-(p-Chlorophenyl)-3-methyl-3-azabicyclo[3.1.0]hexane hydrochloride

To a stirred solution of 11.08 g. of (+)-1-(p-chlorophenyl-1,2-cyclopropanedicarboximide in 50 ml. of anhydrous dimethylformamide is added 2.4 g. of sodium hydride (54% in mineral oil) over 15 minutes under nitrogen. The mixture is stirred for 30 minutes and 5 ml. of iodomethane is added over 5 minutes. The mixture is allowed to stand 15 minutes, is heated on a steam bath 15 minutes, cooled and poured into 125 ml. of water. The mixture is filtered, washed with petroleum ether and dried giving colorless crystals of (+)-N- methyl-1-(p-chlorophenyl)-1,2-cyclopropanedicarboximide.

To a stirred solution of 3.92 g. of (+)-N-methyl-1-(p-chlorophenyl)-1,2-cyclopropanedicarboximide in 100 ml. of benzene under nitrogen is added 20 ml. of Vitride ® during 10 minutes. The mixture is stirred for 2 hours at room temperature and then refluxed for 2 hours. A 20 ml. portion of 10 N sodium hydroxide is added cautiously. the benzene layer is washed with water, dried over magnesium sulfate and evaporated under reduced pressure giving an oil. The oil is dissolved in 200 ml. of ether and saturated with dry hydrogen chloride giving a colorless crystalline cake which is recrystallized from acetonitrile to give (+)-1-(p-chlorophenyl)-3-methyl-3-azabicyclo[3.1.0]hexane hydrochloride as pale tan crystals, m.p. 209°–210° C., $[\alpha]_D^{C-H3OH} = +67°$.

EXAMPLE 9

1-(p-Chlorophenyl)-3-methyl-3-azabicyclo[3.1.0]hexane hydrochloride

To a stirred solution of 44.2 g. of racemic 1-(p-chlorophenyl)-1,2-cyclopropanedicarboximide in 200 ml. of anhydrous dimethylformamide is added 10.0 g. of sodium hydride (50% in mineral oil) over a 5 minute period. A 20 ml. portion of iodomethane is added slowly with stirring over 5 minutes. The mixture is then heated on a steam bath for 30 minutes, cooled and poured into 500 ml. of water. The solid is collected by filtration and recrystallized from heptane-ethyl acetate giving colorless crystals of racemic N-methyl-1-(p-chlorophenyl)-1,2-cyclopropanedicarboximide.

To a stirred solution of 11.8 g. of the above product in 250 ml. of benzene, under nitrogen, is added 60 ml. of Vitride ® over 10 minutes. After standing for 16 hours the mixture is refluxed for 4 hours, cooled and 60 ml. of 10 N sodium hydroxide are cautiously added. The organic layer is dried over sodium sulfate, then magnesium sulfate, filtered and evaporated under reduced pressure to give the free base as a pale yellow oil. The oil is dissolved in 200 ml. of ether and saturated with dry hydrogen chloride gas. The solid is recovered and crystallized from acetonitrile giving pale tan plates, m.p. 180°–182° C.

EXAMPLE 10

3-Benzyl-1-phenyl-3-azabicyclo[3.1.0]heptane hydrochloride

To 37.4 g. of 1-phenyl-1,2-cyclopropanedicarboximide in 200 ml. of anhydrous dimethylformamide is added 10 g. of sodium hydride (50% in mineral oil) with stirring. A 25.4 ml. portion of benzyl chloride is added dropwise. A 20 mg. portion of potassium iodide is added. The mixture is stirred at room temperature for 2 hours and then poured into one liter of water producing a gummy residue which is treated with petroleum ether to produce N-benzyl-1-phenyl-1,2-cyclopropanedicarboximide as pale yellow crystals.

To a stirred solution of 13.87 g. of the above product in 250 ml. of benzene, under nitrogen, is added 60 ml. of Vitride ® over a period of 10 minutes. The mixture is refluxed for 5 hours, cooled and 60 ml. of 10 N sodium hydroxide is added cautiously. The benzene layer is washed with water, dried over magnesium sulfate and evaporated under reduced pressure to an amber oil. The oil is dissolved in ether, dry hydrogen chloride gas is added and the solid is recovered and recrystallized from isopropyl alcohol giving colorless crystals, m.p. 194°–196° C.

EXAMPLE 11

3-Cyclopropylmethyl-1-phenyl-3-azabicyclo[3.1.0]hexane hydrochloride

To a stirred slurry of 61.2 g. of 1-phenyl-1,2-cyclopropanedicarboximide (U.S. Pat. No. 3,166,571, Ex. 8) in 2 liters of benzene is added 400 ml. of Vitride ® under nitrogen. The mixture is stirred at room temperature for 2 hours, refluxed for 4 hours and then stirred at room temperature for 20 hours. A 400 ml. portion of 10 N sodium hydroxide is added cautiously with stirring. The organic layer is washed twice with dilute sodium hydroxide and then with water, dried over magnesium sulfate and evaporated to give an amber oil. This oil is dissolved in dilute hydrochloric acid, washed with ether, filtered and the filtrate made basic with sodium hydroxide. The basic filtrate is extracted with benzene, dried over magnesium sulfate, filtered and evaporated to give 1-phenyl-3-azabicyclo[3.1.0]hexane as an amber oil. To a solution of 15.9 g. of 1-phenyl-3-azabicyclo[3.1.0]hexane in 100 ml. of benzene and 20 ml. of triethylamine is added 11.0 g. of cyclopropanecarboxylic acid chloride in 20 ml. of benzene over 5 minutes. The mixture is stirred for 30 minutes and 50 ml. of water is added. The benzene layer is extracted with dilute sodium bicarbonate followed by dilute hydrochloric acid and then water, dried over magnesium sulfate and evaporated to give the product 3-cyclopropylcarbonyl-1-phenyl-3-azabicyclo[3.1.0]hexane as a brown oil.

To a solution of 11.35 g. of 3-cyclopropylcarbonyl-1-phenyl-3-azabicyclo[3.1.0]hexane in 100 ml. of benzene is added 25 ml. of Vitride ® with stirring. The mixture is allowed to stand for 18 hours, is refluxed for 2 hours, cooled and 25 ml. of 10 N sodium hydroxide is slowly added. The organic layer is washed with saturated sodium chloride, dried over magnesium sulfate and evaporated to a brown oil. This oil is dissolved in ether and dry hydrogen chloride gas is bubbled in producing pink crystals. These crystals are recrystallized for isopropyl alcohol giving pink crystals, m.p. 164°–165° C.

In a like manner 1-(p-tolyl)-3-azabicyclo[3.1.0]hexane (Example 32) is reacted with cyclopropanecarbonyl chloride to give 3-cyclopropanecarbonyl-1-(p-tolyl)-3-azabicyclo[3.1.0]hexane which is reduced as above to give 3-cyclopropylmethyl-1-(p-tolyl)-3-azabicyclo[3.1.0]hexane hydrochloride as colorless crystals, m.p. 180°–182° C.

EXAMPLE 12

3-Phenethyl-1-phenyl-3-azabicyclo[3.1.0]hexane hydrochloride

To a stirred solution of 9.35 g. of 1-phenyl-1,2-cyclopropanedicarboximide in 50 ml. of dimethylformamide is added 2.5 g. of sodium hydride (50% in mineral oil) over 5 minutes. This mixture is warmed and stirred for one-half hour, 0.1 g. of potassium iodide is added and then 9.25 g. of phenethyl bromide is added. This mixture is stirred one-half hour, heated on a steam bath 15 minutes, stirred at room temperature 15 minutes and then poured into one liter of water made acidic with acetic acid. The mixture is extracted with methylene chloride and this solution is combined with 50 g. of magnesium silicate and evaporated under reduced pressure. The residual powder is applied to a magnesium silicate column and eluted with one liter of petroleum ether, 500 ml. of methylene chloride, one liter of chloroform and evaporated giving N-phenethyl-1-phenyl-1,2-cyclopropanedicarboximide as a colorless oil.

To a solution of 5.80 g. of the above compound in 50 ml. of benzene is added 10 ml. of Vitride ® with stirring. The mixture is allowed to stand 18 hours, is refluxed 2 hours, cooled and treated with 10 ml. of 10 N sodium hydroxide as described in Example 1 yielding the crystalline product, m.p. 207°–209° C.

EXAMPLE 13

3-Isopropyl-1-phenyl-3-azabicyclo[3.1.0]hexane hydrochloride

A mixture of 20.6 g. of 1-phenyl-1,2-cyclopropanedicarboxylic acid (U.S. Pat. No. 3,166,571) and 15 g. of 1,3-diisopropylurea in 500 ml. of xylene is refluxed for 6 hours, filtered and the solvent removed under reduced pressure giving an oil. The oil is absorbed on magnesium silicate in 500 ml. of methylene chloride. The solvent is evaporated leaving a powder. The powder is added to magnesium silicate on a buchner funnel and eluted with 500 ml. of petroleum ether and then one liter of methylene chloride. The methylene chloride is evaporated giving N-isopropyl-1-phenyl-1,2-cyclopropanedicarboximide as a colorless oil.

To a solution of 9.17 g. of the above product in 100 ml. of benzene is added 20 ml. of Vitride ® with stirring. The mixture is allowed to stand for 18 hours, is refluxed for 2 hours, cooled and 20 ml. of 10 N sodium hydroxide are slowly added, followed by 30 ml. of 5 N sodium hydroxide. The organic layer is extracted with dilute hydrochloric acid. The aqueous extract is made basic with sodium hydroxide, extracted with ether, dried over magnesium sulfate and dry hydrogen chloride gas is bubbled in producing a gum which is triturated with ether and crystallized from acetone yielding tan crystals, m.p. 141°–144° C.

In a like manner 1-(p-chlorophenyl)-1,2-cyclopropanedicarboxylic acid (U.S. Pat. No. 4,131,611, Ex. 1) and 1,3-diphenylurea give N,1-diphenyl-1,2-cyclopropanecarboximide which is then reduced with Vitride ® to give 1,3-diphenyl-3-azabicyclo[3.1.0]hexane.

EXAMPLE 14

1-(p-Trifluoromethylphenyl)-3-azabicyclo[3.1.0]hexane hydrochloride

Using a method of Example 5, ethyl p-(trifluoromethyl)phenyl acetate is converted to ethyl α-bromo-p-(trifluoromethyl)phenyl acetate and this is reacted with ethyl acrylate-sodium hydride to give diethyl 1-(p-trifluoromethylphenyl)-1,2-cyclopropanedicarboxylate. Hydrolsis with 1 N potassium hydroxide gives cis-1-(p-trifluoromethylphenyl)-1,2-cyclopropanedicarboxylic acid as colorless crystals. This diacid is then reacted with urea to give 1-(p-trifluoromethylphenyl)-1,2-cyclopropanedicarboximide as colorless crystals.

To a solution of 3.5 g. of this imide in 75 ml. of benzene is added 20 ml. of vitride ®. This is refluxed for one hour, cooled to room temperature, and the excess hydride reagent is decomposed with 20 ml. of 10 N sodium hydroxide. The benzene layer is washed with water, dried over magnesium sulfate and evaporated under reduced pressure to give an amber colored oil. This oil is dissolved in ether and dry hydrogen chloride gas is bubbled into the solution. The resultant precipitate is collected by filtration and recrystallized from isopropyl alcohol to give the product, m.p. 249°–251° C.

EXAMPLE 15

3-(p-Chlorobenzyl)-1-(p-chlorophenyl)-3-azabicyclo[3.1.0]hexane

A 19.35 g. portion of 1-p-chlorophenyl-3-azabicyclo[3.1.0]hexane, 10.59 g. of sodium carbonate and 17.5 g. of p-chlorobenzoyl chloride are reacted in benzene. The benzene is evaporated, the dark purple residue is dissolved in 200 ml. of chloroform and washed successively with 5% sodium carbonate, 0.5 N hydrochloric acid and then with water and dried over sodium sulfate giving a dark purple oil. Addition of ether gives the product 3-p-chlorobenzoyl-1-(p-chlorophenyl)-3-azabicyclo[3.1.0]hexane as grey crystals.

A 16.60 g. portion of 3-(p-chlorobenzoyl)-1-(p-chlorophenyl)-3-azabicyclo[3.1.0]hexane is dissolved in 160 ml. of benzene and 55.5 g. of Vitride ® is added dropwise. The mixture is refluxed for 2 hours, cooled and quenched slowly with 10 N sodium hydroxide. Water is added, the organic layer is separated and washed 3 times with water and then dried over magnesium sulfate. Removal of the solvent yields an off-white solid, m.p. 88°–92° C.

In a like manner, reductions of the following amides with Vitride ® yield the corresponding reduced products.

| Amide | Reduction Product |
|---|---|
| A | |
| 3-(2-naphthylcarbonyl)-1-(p-chlorophenyl)-3-azabicyclo[3.1.0]hexane | 3-(2-naphthylmethyl)-1-(p-chlorophenyl)-3-azabicyclo[3.1.0]hexane hydrochloride, m.p. 136–138° C. |
| B | |
| 3-(5-norbornen-2-yclarbonyl)-1-(p-chlorophenyl)-3-azabicyclo[3.1.0]hexane | 3-(5-norbornen-2-yl-methyl-1-(p-chlorophenyl)-3-azabicyclo[3.1.0]hexane hydrochloride, m.p. 214–217° C. |
| C | |
| 3-acetyl-1-(p-aminophenyl)-3-azabicyclo[3.1.0]hexane | 3-ethyl-1-(p-aminophenyl)-3-azabicyclo[3.1.0]hexane |
| D | |
| 1-(p-chlorophenyl)-3-propiolyl-3-azabicyclo[3.1.0]hexane | 1-(p-chlorophenyl)-3-propargyl-3-azabicyclo[3.1.0]hexane |

The above intermediates A, B, and D are prepared by acylation of the corresponding 3-azabicyclo[3.1.0]hexanes with the appropriate acid chloride, as described in Example 15.

The compound 3-acetyl-1-(p-aminophenyl)-3-azabicyclo[3.1.0]hexane is prepared by acetylation of 1-p-nitrophenyl)-3-azabicyclo[3.1.0]hexane (Example 30), as in Example 15, followed by reduction with palladium on charcoal in tetrahydrofuran.

EXAMPLE 16

3-(1-Adamantylmethyl)-1-(p-chlorophenyl)-3-azabicyclo[3.1.0]hexane

A 19.35 g. portion of 1-p-chlorophenyl-3-azabicyclo[3.1.0]hexane, 10.59 g. of sodium carbonate and 19.87 g. of 1-adamantanecarboxylic acid chloride are reacted in accordance with Example 32 yielding the product 3-(1-adamantylcarbonyl)-1-(p-chlorophenyl)-3-azabicyclo[3.1.0]hexane as a white solid, m.p. 163°–165° C.

A 17.77 g. portion of 3-(1-adamantylcarbonyl)-1-(p-chlorophenyl-3-azabicyclo[3.1.0]hexane, is treated as described in Example 15 yielding a yellow oil which crystallizes to a white solid on standing, m.p. 72°–75° C.

EXAMPLE 17

3-Allyl-1-phenyl-3-azabicyclo[3.1.0]hexane hydrochloride

To 18.7 g. of 1-phenyl-1,2-cyclopropanedicarboximide in 100 ml. of dimethylformamide is added 5 g. of sodium hydride (50% in mineral oil). The mixture is warmed on a steam bath and 9 ml. of allyl bromide is added over 5 minutes with stirring. This mixture is heated on a steam bath for one-half hour, then at room temperature for 2 hours, poured into one liter of water and extracted with methylene chloride. The organic layer is mixed with 50 g. of magnesium silicate and evaporated on a rotary evaporator. This mixture is then added to 200 g. of magnesium silicate in a Buchner funnel and eluted with one liter of petroleum ether and then one liter of chloroform. The chloroform fraction is evaporated under reduced pressure giving N-allyl-1-phenyl-1,2-cyclopropanedicarboximide as a colorless oil.

To a solution of 8.0 g. of the above product in 70 ml. of benzene is added 17.5 ml. of Vitride ®. The mixture is refluxed for 2 hours and then stirred at room temperature for 2 hours. Processing as described in Example 15 yields the desired product, m.p. 124°–128° C.

In a like manner, 1-(p-tolyl)-1,2-cyclopropanedicarboximide (Example 32) is reacted with allyl bromide to give N-allyl-1-(p-tolyl)-1,2-cyclopropanedicarboximide which is then reduced as above to give 3-allyl-1-(p-tolyl)-3-azabicyclo[3.1.0]hexane hydrochloride as colorless crystals, m.p. 165°–167° C.

In a like manner, 1-(p-tolyl)-1,2-cyclopropanedicarboximide (Example 32) is reacted with propargyl bromide to give N-propargyl-1-(p-tolyl)-1,2-azacyclopropanedicarboximide which is then reduced as above to give 3-propargyl-1-(p-tolyl)-3-azabicyclo[3.1.0]hexane hydrochloride.

EXAMPLE 18

3-Ethyl-1-phenyl-3-azabicyclo[3.1.0]hexane hydrochloride

To 15.9 g. of 1-phenyl-3-azabicyclo[3.1.0]hexane in 20 ml. of pyridine is added 20 ml. of acetic anhydride. The mixture is allowed to stand overnight at room temperature and then evaporated to give an oil. This oil is dissolved in a mixture of ether and methylene chloride, washed with dilute hydrochloric acid and then sodium bicarbonate, dried over magnesium sulfate and evaporated to a pale amber liquid. This liquid is crystallized from hexane to give the product 3-acetyl-1-phenyl-3-azabicyclo[3.1.0]hexane, m.p. 63°–65° C.

A 10.0 g. portion of 3-acetyl-1-phenyl-3-azabicyclo[3.1.0]hexane, in 100 ml. of benzene is treated with 25 ml. of Vitride ® as described in Example 15, yielding tan crystals, m.p. 148°–152° C.

EXAMPLE 19

3-(Cyclohexylmethyl)-1-phenyl-3-azabicyclo[3.1.0]hexane hydrochloride

A 6.4 g. portion of 1-phenyl-3-azabicyclo[3.1.0]hexane is added to 60 ml. of benzene. A 4.2 g. portion of sodium carbonate in 40 ml. of water is added with stirring. A 5.9 a. portion of cyclohexylcarbonyl chloride in 40 ml. of benzene is added and the mixture is stirred overnight. The oily solid in the aqueous layer is extracted with chloroform. The extracts are washed with water and dilute hydrochloric acid, dried over magnesium sulfate, filtered and evaporated. The oily residue is extracted with ether giving a white solid as the product 3-cyclohexylcarbonyl-1-phenyl-3-azabicyclo[3.1.0]hexane, m.p. 81°–82° C.

A 7.0 g. portion of 3-cyclohexylcarbonyl-1-phenyl-3-azabicyclo[3.1.0]hexane, in 50 ml. of benzene is treated with 13 ml. of Vitride ® and 13 ml. of 10 N sodium hydroxide, as described in Example 15, yielding the hydrochloride as colorless crystals, m.p. 215°–218° C.

EXAMPLE 20

1-(p-Methoxyphenyl)-3-azabicyclo[3.1.0]hexane hydrochloride

A mixture of 2.6 g. of diethyl 1-(p-methoxyphenyl)-1,2-cyclopropanedicarboxylate (prepared by the method of Example 5 from ethyl-p-methoxyphenylacetate), 20 ml. of 1 N potassium hydroxide and 20 ml. of ethanol is refluxed 3.5 hours and the ethanol is removed by concentrating. A 20 ml. portion of 1 N hydrochloric acid is added and then incremental portions of acid are added until the pH is one. The mixture is extracted three times with chloroform, dried and concentrated to a yellow solid. This solid is recrystallized from ethyl acetate-hexane to give cis-1-(p-methoxyphenyl)-1,2-cyclopropanedicarboxylic acid as a pale yellow solid.

A 6.6 g. portion of this diacid, 2.4 g. of urea and 300 ml. of xylene is refluxed and stirred for 24 hours. The mixture is cooled, diluted with 25 ml. of benzene, washed with water, dried and concentrated under reduced pressure to give a solid which is recrystallized from ethyl acetate-hexane to give 1-(p-methoxyphenyl)-1,2-cyclopropanedicarboximide.

A 3.0 g. portion of the above product is mixed with 70 ml. of benzene and 20 ml. of Vitride ® is added over a 5 minute period with stirring. After stirring for one-half hour and refluxing for one hour the mixture is cooled and 20 ml. of 10 N sodium hydroxide is added followed by saturated sodium chloride. The organic layer is dried over magnesium sulfate, filtered and evaporated to an oil. The oil is dissolved in ether and hydrogen chloride gas is bubbled in. The solid which forms is recrystallized from isopropyl alcohol giving pale pink plates, m.p. 174°–175° C.

EXAMPLE 21

(+)-1-Phenyl-3-azabicyclo[3.1.0]hexane hydrochloride

To a stirred slurry of 10 g. of (+)-1-phenyl-1,2-cyclopropanedicarboximide (J. Med. Chem. 24:481) in 300 ml. of benzene under nitrogen is added 80 ml. of Vitride ®. The mixture is stirred at room temperature for 2 hours, refluxed for 4 hours, stirred at room temperature for 20 hours and then 80 ml. of 10 N sodium hydroxide is added slowly with stirring. The organic layer is washed with saturated sodium chloride, water, dried over magnesium sulfate and filtered. The filtrate is evaporated, ether is added and dry hydrogen chloride gas is bubbled in. The product is recovered by filtration and recrystallized from acetonitrile giving colorless needles, m.p. 169°–171° C., $[\alpha]_D^{CH_3OH} = +68°$.

EXAMPLE 22

1-(p-Chlorophenyl)-3-(o-fluorobenzyl)-3-azabicyclo[3.1.0]hexane hydrochloride A 19.53 g. portion of 1-(p-chlorophenyl)-3-azabicyclo[3.1.0]hexane, 10.59 g. of sodium carbonate and 15.8 g. of o-fluorobenzoyl chloride are reacted to give the product 3-(o-fluorobenzoyl)-1-(p-chlorophenyl)-3-azabicyclo[3.1.0]hexane as a brown gum.

A 13.9 g. portion of 3-(o-fluorobenzoyl)-1-(p-chlorophenyl)-3-azabicyclo[3.1.0]hexane is reacted as described in Example 15 with 50 ml. of Vitride ® yielding a light yellow oil. This base is treated with ethanolic hydrochloric acid and ether to give the hydrochloride as a white solid, m.p. 204°-206° C.

In a similar manner, 3-(p-fluorobenzoyl)-1-phenyl-3-azabicyclo[3.1.0]hexane is reduced by Vitride ® to give 3-(p-fluorobenzyl)-1-phenyl-3-azabicyclo[3.1.0]hexane.

Likewise, 3-(m-fluorobenzoyl)-1-(p-chlorophenyl)-3-azabicyclo[3.1.0]hexane is prepared from 1-(p-chlorophenyl)-3-azabicyclo[3.1.0]hexane and m-fluorobenzoylchloride, then converted as above to 3-(m-fluorobenzyl)-1-(p-chlorophenyl)-3-azabicyclo[3.1.0]hexane hydrochloride, m.p. 241°-244° C.

EXAMPLE 23

1-(3,4-Dichlorophenyl)-3-azabicyclo[3.1.0]hexane hydrochloride

A solution of 59.5 g. of 3,4-dichlorophenylacetic acid in 500 ml. of absolute ethanol is saturated with anhydrous hydrogen chloride and then heated at reflux for 2 hours. The mixture is concentrated under reduced pressure to 200 ml., diluted with 200 ml. of water and neutralized with concentrated ammonium hydroxide. This aqueous mixture is extracted 3 times with chloroform. Concentration and decolorization of the chloroform extracts gives ethyl 3,4-dichlorophenylacetate as a yellow oil.

In a three-necked flask fitted with a Nichrome stirrer and a relux condenser is placed 7.0 g. of ethyl 3,4-dichlorophenylacetate, 5.9 g. of N-bromosuccinimide, 0.1 g. of benzoyl peroxide and 150 ml. of carbon tetrachloride. The reaction mixture is heated at reflux for 18 hours, cooled and filtered. The carbon tetrachloride filtrate is concentrated under reduced pressure to give a deep orange liquid. Vacuum distillation at 115°-120° C. (0.5 mm) gives ethyl α-bromo-3,4-dichlorophenylacetate as a pale yellow liquid.

This product is converted to diethyl cis-1-(3,4-dichlorophenyl)-1,2-cyclopropanedicarboxylate by the method of L. L. McCoy, J. A. C. S. 80: 6568 (1958).

A mixture of 150 g. of this diester and 66 g. of 85% potassium hydroxide in 500 ml. of water and 500 ml. of ethanol is refluxed for 6 hours and then chilled in ice. The oily material is extracted into ether and the aqueous layer is made acidic with 100 ml. of 12 N hydrochloric acid. The oily lower layer crystallizes slowly to give a colorless crystalline cake. This is recrystallized from a mixture of ethanol and ethyl acetate to give colorless crystals of 1-(3,4-dichlorophenyl)-1,2-cyclopropanedicarboxylic acid.

A mixture of 30.3 g. of this diacid and 12.6 g. of urea in one liter of xylene is refluxed for 6 hours. The solvent is stripped under reduced pressure and the crystalline residue is slurried with water. The colorless crystals are collected by filtration, washed with water and air dried to give 1-(3,4-dichlorophenyl)-1,2-cyclopropanedicarboximide.

To 40 ml. of one molar borane-tetrahydrofuran is added, with stirring under nitrogen at 0° C., a solution of 2.56 g. of this imide in 50 ml. of tetrahydrofuran during 15 minutes. The solution is warmed in a steam bath for one hour and is then cooled in ice. Then 20 ml. of 6 N hydrochloric acid is added, and the tetrahydrofuran is removed under reduced pressure. The residue is made basic with 75 ml. of 5 N sodium hydroxide and this is extracted with ether. The extract is dried over magnesium sulfate, filtered, and the filtrate is saturated with hydrogen chloride. The precipitated crystals are collected by filtration and are recrystallized from isopropyl alcohol to give 1.70 g. of 1-(3,4-dichlorophenyl)-3-azabicyclo[3.1.0]hexane hydrochloride as colorless crystals, m.p. 180°-181° C.

The following imides, prepared in the above manner, are likewise reduced to the corresponding 3-azabicyclo[3.1.0]hexanes:

| Imide | Reduction Product |
| --- | --- |
| 1-(p-ethylphenyl)-1,2-cyclopropanedicarboximide | 1-(p-ethylphenyl)-3-azabicyclo[3.1.0]hexane hydrochloride, m.p. 207–209° C. |
| 1-(p-hexylphenyl)-1,2-cyclopropanedicarboximide | 1-(p-hexylphenyl)-3-azabicyclo[3.1.0]hexane hydrochloride, m.p. 181–183° C. |
| 1-(m-tolyl)-1,2-cyclopropanedicarboximide | 1-(m-tolyl)-3-azabicyclo[3.1.0]hexane hydrochloride, m.p. 129–131° C. |
| 1-(p-bromophenyl)-1,2-cyclopropanedicarboximide | 1-(p-bromophenyl)-3-azabicyclo[3.1.0]hexane hydrochloride, m.p. 231–233° C. |
| 1-(p-fluorophenyl)-1,2-cyclopropanedicarboximide | 1-(p-fluorophenyl)-3-azabicyclo[3.1.0]hexane hydrochloride, m.p. 170–172° C. |

In the above manner, N-benzoyl-1-(p-bromophenyl)-1,2-cyclopropanedicarboximide, made by reaction of 1-(p-bromophenyl)-1,2-cyclopropanedicarboximide with benzyl chloride, as in Example 10 is converted to 3-benzyl-1-(p-bromophenyl)-3-azabicyclo[3.1.0]hexane, m.p. 69°-70° C.

EXAMPLE 24

1-(m-Methoxyphenyl)-3-methyl-3-azabicyclo[3.1.0]hexane hydrochloride

A 92.3 g. portion of m-anisidine is dissolved in 225 ml. of concentrated hydrochloric acid, 150 ml. of water and 150 g. of ice and cooled to 0° C. This mixture is diazotized carefully with vigorous stirring at 0°-5° C. with 52.5 g. of sodium nitrite in 120 ml. of water. This mixture is then added to 83.25 g. of N-methylmaleimide in 225 ml. of acetone at 0° C. The pH is adjusted to 3.0 and 25.5 g. of cuprous chloride dihydrate is added in one portion followed by 200 ml. of acetone, with stirring. Evaporation of the acetone and decantation of the aqueous layer leaves a black residue which is boiled with one liter of benzene, dried over magnesium sulfate and filtered through a Buchner funnel containing 50 g. of activated magnesium silicate. The residue is boiled with one liter of benzene and filtered through activated magnesium silicate. The dark filtrate is evaporated under reduced pressure and then heated for 10 minutes with 100 ml. of 2,6-lutidine to insure dehydrochlorination.

This solution is combined with 500 ml. of water and 400 ml. of pyridine and filtered. The crystalline cake is pressed free of dark oil and then boiled with 500 ml. of 90% ethanol. This is cooled and filtered giving 2-(m-methoxyphenyl)-N-methylmaleimide as orange crystals.

This product is converted to 1-(m-methoxyphenyl)-N-methyl-1,2-cyclopropanedicarboximide by the method of P. T. Izzo, J. Organic Chemistry 28: 1713 (1963).

To a mixture of 3.0 g. of this imide in 70 ml. of benzene is added 20 ml. of Vitride ® over a 5 minute period under nitrogen with stirring. The mixture is stirred for 30 minutes, refluxed for one hour, cooled and 20 ml. of 10 N sodium hydroxide and then saturated sodium chloride are added. The organic layer is dried over magnesium sulfate, filtered and evaporated giving crystals, which are recrystallized from ether. Reaction with hydrogen chloride gas and recrystallization from isopropyl alcohol gives the crystalline product 1-(m-methoxyphenyl)-3-methyl-3-azabicyclo[3.1.0]hexane hydrochloride, m.p. 148°–150° C.

EXAMPLE 25

(+)-3-Methyl-1-phenyl-3-azabicyclo[3.1.0]hexane hydrochloride

A mixture of 10 g. of (+)-1-phenyl-1,2-cyclopropanedicarboximide (J. Med. Chem. 24:481), 2.67 g. of sodium hydride (50% in mineral oil), 50 ml. of dimethylformamide and 5 ml. of methyl iodide is reacted and poured into 500 ml. of water. This mixture is extracted with methylene chloride, washed with water, dried over magnesium sulfate, and evaporated. The residue is adsorbed on activated magnesium silicate in a Buchner funnel and washed with 250 ml. of benzene. The eluate is washed with 500 ml. of methylene chloride and evaporated giving green crystals, of (+)-1-phenyl-N-methyl-1,2-cyclopropanedicarboximide.

A 3.0 g. portion of this imide in 70 ml. of dry benzene is reacted with 20 ml. of Vitride ®. The mixture is stirred for 15 minutes at room temperature and then on a steam bath for 15 minutes. After cooling the reaction mixture is treated as described in Example 8 giving (+)-1-phenyl-3-methyl-3-azabicyclo[3.1.0]hexane hydrochloride as crystals, m.p. 188°–190° C., $[\alpha]_D^{C-H_3OH} = +72°$.

EXAMPLE 26

1-(p-Chloro-α,α,α-trifluoro-m-tolyl)-3-azabicyclo[3.1.0]hexane hydrochloride

Using the method of Example 5, methyl(p-chloro-α,α,α-trifluoro-m-tolyl)acetate is converted to methyl bromo(p-chloro-α,α,α-trifluoro-m-tolyl)acetate, and this is reacted with methyl acrylate-sodium hydride to give dimethyl 1-(p-chloro-α,α,α-trifluoro-m-tolyl)cyclopropanedicarboxylate. Hydrolysis with 1 N potassium hydroxide gives cis-1-(p-chloro-α,α,α-trifluoro-m-tolyl)-1,2-cyclopropanedicarboxylic acid as colorless crystals, and the diacid is then reacted with urea to give 1-(p-chloro-α,α,α-trifluoro-m-tolyl)-1,2-cyclopropanedicarboximide as colorless crystals.

To a solution of 0.28 g. of 1-(p-chloro-α,α,α-trifluoro-m-tolyl)cyclopropanedicarboximide in 10 ml. of benzene is added one ml. of Vitride ®. This is refluxed for one hour, cooled to ambient temperature, and the excess hydride reagent is decomposed with one ml. of 10 N sodium hydroxide. The benzene layer is washed with water, dried over magnesium sulfate and evaporated under reduced pressure to give an amber-colored oil. This is dissolved in ether and dry hydrogen chloride is bubbled into the solution. The resultant precipitate is collected by filtration and recrystallized from isopropyl alcohol to give 1-(p-chloro-α,α,α-trifluoro-m-tolyl)-3-azabicyclo[3.1.0]hexane hydrochloride. Purification of the hydrochloride by recrystallization from acetonitrile gives colorless crystals, m.p. 164°–166° C.

EXAMPLE 27

3,6-Dimethyl-1-phenyl-3-azabicyclo[3.1.0]hexane hydrochloride

To a stirred solution of N,3-dimethylcyclopropane-1,2-dicarboximide (U.S. Pat. No. 3,166,571, Ex. 2) in benzene is added Vitride ® for several minutes. This solution is stirred at ambient temperature for several hours, refluxed for one hour, and then cooled and combined with sodium hydroxide and worked-up and converted to the hydrochloride to give the title product.

EXAMPLE 28

1-(p-Acetamidophenyl)-3-ethyl-3-azabicyclo[3.1.0]hexane

To a suspension of 3-ethyl-1-(p-aminophenyl)-3-azabicyclo[3.1.0]hexane (Example 15) in aqueous sodium acetate is added acetic anhydride. This is heated on a steam bath for several minutes and filtered to give the product.

EXAMPLE 29

1-(m-Hydroxyphenyl)-3-methyl-3-azabicyclo[3.1.0]hexane

A solution of 1-(m-methoxyphenyl)-3-methyl-3-azabicyclo[3.1.0]hexane in 48% hydrobromic acid is refluxed for several hours and the solution is made basic with sodium bicarbonate. The desired phenol is collected by filtration.

EXAMPLE 30

1-(p-Nitrophenyl)-3-azabicyclo[3.1.0]hexane hydrochloride

To a stirred slurry of 20.6 g. of 1-phenylcyclopropane-1,2-dicarboxylic acid (J. Med. Chem. 24:481) in 25 ml. of concentrated sulfuric acid at 0° C. is added 15 ml. of concentrated nitric acid over 30 minutes. The resultant solution is stirred at ambient temperature for 30 minutes and then poured onto ice. The crystalline product is recrystallized from hexane-ethyl acetate to give 1-(p-nitrophenyl)-cyclopropane-1,2-dicarboxylic acid as colorless crystals.

The above diacid is converted to 1-(p-nitrophenyl)-1,2-cyclopropane-dicarboximide, m.p. 171°–173° C., by the method described in Example 5.

A solution of the above imide in tetrahydrofuran is added to a 1 M solution of borane-tetrahydrofuran at 0° C., under nitrogen. The solution is refluxed for one hour, cooled to 0° C. and then 6 N hydrochloric acid is added. Tetrahydrofuran is removed under reduced pressure and the residual material is distributed between ether and sodium hydroxide. The ether solution, containing 1-(p-nitrophenyl)-3-azabicyclo[3.1.0]hexane, is dried over magnesium sulfate, filtered, and to the filtrate is added hydrogen chloride to give the product as a brown solid, m.p. 215°–217° C.

EXAMPLE 31

1-(o-Chlorophenyl)-3-azabicyclo[3.1.0]hexane hydrochloride

A stirred mixture of 36.9 g. of methyl o-chlorophenylacetate, 36.0 g. of N-bromosuccinimide, and 2 drops of 48% hydrobromic acid in 500 ml. of carbon tetrachloride is refluxed for 20 hours and then filtered through magnesium silicate. Evaporation under reduced pressure gives methyl α-bromo-o-chlorophenylacetate as a straw-colored liquid.

To a stirred suspension of 4.8 g. of sodium hydride (50% in mineral oil) in 100 ml. of benzene-N,N-dimethylformamide (1:1) is added a mixture of 26.3 g. of the above bromoester and 8.69 g. of methyl acrylate over ½ hour. The mixture is stirred at ambient temperature for 4 hours, excess sodium hydride is then decomposed with 2 ml. of methanol, and this mixture is poured into 500 ml. of water. The organic layer is washed with water, dried over magnesium sulfate, and evaporated to give dimethyl-1-(o-chlorophenyl)-1,2-cyclopropanedicarboxylate as a brown oil.

The above diester (17.35 g.) and 200 ml. of 1 N potassium hydroxide in 50 ml. of ethanol is refluxed for 6 hours. The solution is reduced to one-half volume under reduced pressure and acidified to give 1-(o-chlorophenyl)-1,2-cyclopropanedicarboxylic acid as a brown oil.

A mixture of 10.0 g. of the above diacid and 3.4 g. of urea in 500 ml. of xylene is refluxed for 6 hours. The solution is washed with water and sodium bicarbonate and then dried over magnesium sulfate to give a tan solid. Recrystallization from ethanol gives 1-(o-chlorophenyl)-1,2-cyclopropanedicarboximide as colorless crystals.

To 1.35 g. of the above imide in 30 ml. of benzene is added 9 ml. of Vitride ® over 2 minutes with stirring. The solution is stirred at ambient temperature for 15 minutes and is then refluxed for 30 minutes. To the cooled solution is added 10 ml. of 10 N sodium hydroxide and the benzene layer is washed with water, dried over magnesium sulfate and filtered. The filtrate is evaporated under reduced pressure, the residual oil is dissolved in ether and to this solution is added anhydrous hydrogen chloride gas. The precipitated product is recrystallized from isopropyl alcohol to give 1-(o-chlorophenyl)-3-azabicyclo[3.1.0]hexane hydrochloride as colorless crystals, m.p. 188°–190° C.

EXAMPLE 32

1-(p-Tolyl)-3-azabicyclo[3.1.0]hexane hydrochloride

To 120 g. of p-tolylacetic acid is added 230 ml. of thionyl chloride and the solution is allowed to stand at room temperature for 2 hours, after which it is warmed to 60° C. for one hour. To this solution is added 285 g. of N-bromosuccinimide and 10 drops of 48% hydrobromic acid and the mixture is then refluxed on a 90° C. oil bath for one hour. An additional 90 ml. of thionyl chloride is added and refluxing continued for 45 minutes. The mixture is distilled under reduced pressure to remove 250 ml. of thionyl chloride, and the residual liquid is poured into 500 ml. of cold methanol with stirring and ice cooling over 15 minutes. This solution is evaporated under reduced pressure to give a dark oil which is dissolved in 100 ml. of chloroform. The solution is washed with 500 ml. of water, dried over magnesium sulfate and filtered. The filtrate is evaporated under reduced pressure to give a dark oil which is distilled to give 94 g. of bromoester as a pale yellow liquid. The pale yellow liquid is then reacted with methyl acrylate-sodium hydride in ether (as in Example 5) to give dimethyl cis-1-(p-tolyl)-1,2-cyclopropanedicarboxylate. Hydrolysis with 1 N potassium hydroxide, followed by acidification with hydrochloric acid (as in Example 5), gives cis-1-(p-tolyl)-1,2-cyclopropanedicarboxylic acid as colorless crystals. This diacid is then reacted with urea (as in Example 5) to give 1-(p-tolyl)-1,2-cyclopropanedicarboximide as pale yellow crystals.

To a mixture of 20.1 g. of this imide in 600 ml. of benzene is added 160 ml. of Vitride ® and the reaction is run as in Example 7. Then the excess reagent is decomposed with 160 ml. of 10 N sodium hydroxide. The benzene layer is washed with water, dried over magnesium sulfate and filtered. The filtrate is evaporated under reduced pressure to give a dark oil which is dissolved in ether, and then dry hydrogen chloride is bubbled into the solution. The resultant precipitate is collected by filtration and recrystallized from acetonitrile-methanol to give 12.1 g. of 1-(p-tolyl)-3-azabicyclo[3.1.0]hexane hydrochloride as pale tan plates, m.p. 207°–208° C.

In the same manner 1-(p-isopropylphenyl)-1,2-cyclopropanedicarboximide gives 1-(p-isopropylphenyl)-3-azabicyclo[3.1.0]hexane hydrochloride, m.p. 231°–232° C.

The following imides are reduced in the above manner to give the corresponding amine hydrochloride:

| Imide | 3-Azabicyclo[3.1.0]hexane |
|---|---|
| 1-(α,α,α-trifluoro-m-tolyl)-1,2-cyclopropanedicarboximide | 1-(α,α,α-trifluoro-m-tolyl)-3-azabicyclo[3.1.0]hexane hydrochloride, m.p. 146–148° C. |
| 1-(α,α,α-trifluoro-p-tolyl)-1,2-cyclopropanedicarboximide | 1-(α,α,α-trifluoro-p-tolyl)-3-azabicyclo[3.1.0]hexane hydrochloride, m.p. 249–251° C. |
| 1-(3-bromo-4-methoxyphenyl)-1,2-azacyclopropanedicarboximide | 1-(3-bromo-4-methoxyphenyl)-3-azabicyclo[3.1.0]hexane hydrochloride, m.p. 108–211° C. |
| 1-(p-cyclohexylphenyl)-1,2-cyclopropanedicarboximide | 1-(p-cyclohexylphenyl)-3-azabicyclo[3.1.0]hexane |
| 1-(4-biphenyl)-1,2-cyclopropanedicarboximide | 1-(4-biphenyl)-3-azabicyclo[3.1.0]hexane hydrochloride m.p. 268–270° C. |

EXAMPLE 33

(+)-1-(p-Tolyl)-3-azabicyclo[3.1.0]hexane hydrochloride

A solution of 94.8 g. of racemic-1-(p-tolyl)-1,2-cyclopropanedicarboxylic acid (Example 32) and 73.8 g. of (−)-α-(1-naphthyl)ethylamine in 300 ml. of tetrahydrofuran is diluted with 300 ml. of ethyl ether and allowed to stand at room temperature until crystallization is complete. The mixture is filtered and the crystals which are collected are washed with cold tetrahydrofuran to give 49.5 g. of a salt comprised of one molar equivalent of (+)-1-(p-tolyl)-1,2-cyclopropanedicarboxylic acid and one molar equivalent of (−)-α-(1-naphthyl)ethylamine. The salt is shaken with sodium hydroxide solution and ether. The aqueous phase is acidified with 12 N hydrochloric acid and the product is collected by filtration to give 26.0 g. of (+)-1-(p-tolyl)-1,2-cyclopropanedicarboxylic acid as colorless crystals, $[\alpha]_D^{C_2H_3OH} = +192°$.

A 15.0 g. portion of (+)-1-(p-tolyl)-1,2-cyclopropanedicarboxylic acid, 6.6 g. of urea and 500 ml. of xylene is refluxed and stirred for 5 hours. The reaction mixture is then filtered hot and the filtrate is evaporated under reduced pressure to give (+)-1-(p-tolyl)-1,2-cyclopropanedicarboximide as colorless crystals.

A 14 g. portion of the above product is mixed with 420 ml. of benzene and 112 ml. of Vitride ® is added over a 15 minute period with stirring. After refluxing for 1½ hours the mixture is cooled and 160 ml. of 10 N sodium hydroxide are added. The organic layer is dried over sodium sulfate, filtered and evaporated to an oil. The oil is dissolved in ether and hydrogen chloride gas is bubbled in. The solid which forms is recrystallized from acetonitrile giving (+)-1-(p-tolyl)-3-azabicyclo[3.1.0]hexane hydrochloride as colorless crystals, m.p. 208°–210.5° C., $[\alpha]_D^{CH_3OH} = +64.5°$.

The above racemic-diacid is combined with an equimolar amount of brucine in ethanol to give a salt comprised of one molar equivalent of (−)-1-(p-tolyl)-1,2-cyclopropanedicarboxylic acid and one equivalent of brucine, $[\alpha]_D^{CH_3OH} = -46°$. Treatment of this salt, as above, gives (−)-1-(p-tolyl)-1,2-cyclopropanedicarboxylic acid as colorless crystals, $[\alpha]_D^{CH_3OH} = -189°$.

In the above manner, (−)-1-(p-tolyl)-1,2-cyclopropanedicarboxylic acid (U.S. Pat. No. 4,118,417, Ex. 2) is converted to (−)-1-(p-tolyl)-1,2-cyclopropanedicarboximide, m.p. 145°–148° C., $[\alpha]_D^{C_2H_3OH} = -74°$, and this is then reduced as above to give (−)-1-(p-tolyl)-3-azabicyclo[3.1.0]hexane hydrochloride as colorless crystals, m.p. 204°–207° C., $[\alpha]_D^{C_2H_3OH} = -64°$.

EXAMPLE 34

3-Methyl-1-(p-tolyl)-3-azabicyclo[3.1.0]hexane hydrochloride.

A mixture of 4.19 g. of 1-(p-tolyl)-3-azabicyclo[3.1.0]hexane hydrochloride and 20 ml. of water is made basic with sodium hydroxide. This mixture is extracted with ether and the ether is evaporated to give an oil. This oil is combined with 40 ml. of 97% formic acid and 35 ml. of 37% formaldehyde and the solution is heated on a steam bath for 2 hours. The solution is cooled, made basic with sodium hydroxide and extracted with ether. The extract is dried over magnesium sulfate, filtered, and the filtrate is saturated with hydrogen chloride. The precipitated crystals are collected and recrystallized from isopropyl alcohol to give 3-methyl-1-(p-tolyl)-3-azabicyclo[3.1.0]hexane hydrochloride as colorless crystals, m.p. 197°–198° C.

The following amines are converted to the N-methyl derivative in the above manner.

| Amine | N—Methyl Derivative |
|---|---|
| (+)-1-(p-tolyl)-3-azabicyclo[3.1.0]hexane | (+)-3-methyl-1-(p-tolyl)-3-azabicyclo[3.1.0]hexane |
| (−)-1-(p-tolyl)-3-azabicyclo[3.1.0]hexane | (−)-3-methyl-1-(p-tolyl)-3-azabicyclo[3.1.0]hexane |

EXAMPLE 35

1-(p-Hydroxyphenyl)-3-azabicyclo[3.1.0]hexane hydrochloride

To a slurry of 7.2 g. of sodium hydride (50% oil dispersion) in 170 ml. of N,N-dimethylformamide at 0°–5° C. is added a solution of 10.1 ml. of ethanethiol in 85 ml. of N,N-dimethylformamide over a 15 minute period. An additional 3.16 g. portion of sodium hydride is added followed by 14.4 g. of 1-(p-methoxyphenyl)-3-azabicyclo[3.1.0]hexane hydrochloride. After the addition of 40 ml. of N,N-dimethylformamide, the mixture is refluxed for 4 hours and the solvent is then removed. The residue is dissolved in 150 ml. of water and mineral oil and extracted with ether. The aqueous solution is made acidic with acetic acid and the precipitated crystals are collected by filtration to give 9.8 g. of 3-formyl-1-(p-hydroxyphenyl)-3-azabicyclo[3.1.0]hexane as tan crystals, m.p. 166°–167° C.

A solution of 4.50 g. of the above N-formyl derivative in 40 ml. of 1.25N sodium hydroxide is heated on a steam bath for 3 hours under nitrogen. The chilled solution is neutralized with acetic acid and filtered to give 3.30 g. of the amine as a tan powder, m.p. 174°–177° C. This is dissolved in 20 ml. of absolute ethanol and hydrogen chloride gas is bubbled into the solution. Evaporation of the liquid gives 3.78 g. of (p-hydroxyphenyl)-3-azabicyclo[3.1.0]hexane hydrochloride as tan crystals, m.p. 195°–196° C.

EXAMPLE 36

1-(m-Hydroxyphenyl)-3-azabicyclo[3.1.0]hexane hydrochloride

In the manner of Example 35 1-(m-methoxyphenyl-3-azabicyclo[3.1.0]hexane hydrochloride is converted to 3-formyl-1-(m-hydroxyphenyl)-3-azabicyclo[3.1.0]hexane, m.p. 129°–130° C. This is hydrolyzed with sodium hydroxide, as described above, to give 1-(m-hydroxyphenyl)-3-azabicyclo[3.1.0]hexane hydrochloride as pale tan crystals, m.p. 209°–210° C.

EXAMPLE 37

1-(p-Ethoxyphenyl)-3-azabicyclo[3.1.0]hexane hydrochloride

To a stirred mixture of 1.0 g. of 3-formyl-1-(p-hydroxyphenyl)-3-azabicyclo[3.1.0]hexane and 0.7 g. of potassium carbonate in 25 ml. of absolute ethanol is added a solution of 3.2 g. of ethyl iodide in 10 ml. of absolute ethanol. The mixture is refluxed for 2 hours and then is filtered and evaporated. The residual mixture of crystals and liquid is combined with water and this is extracted with chloroform. The extract is dried over magnesium sulfate and evaporated to give 1.0 g. of a colorless, viscous liquid, which crystallizes on standing. Recrystallization from hexane gives 0.31 g. of 3-formyl-1-(p-ethoxyphenyl)-3-azabicyclo[3.1.0]hexane as colorless crystals, m.p. 48°–51° C.

A solution of 2.0 g. of this compound in 50 ml. of ethanol and 20 ml. of 5 N sodium hydroxide is heated on a steam bath for 30 minutes and the ethanol is then removed under reduced pressure. The residue is extracted with ether, the extract is dried over magnesium sulfate, filtered, and then is evaporated to give 1-(p-ethoxyphenyl)-3-azabicyclo[3.1.0]hexane as colorless crystals, m.p. 48°–49° C. This is combined with ethanolic hydrogen chloride to give 1-(p-ethoxyphenyl)-3-azabicyclo[3.1.0]hexane hydrochloride as colorless crystals, m.p. 192°–193° C.

EXAMPLE 38

1-Phenyl-3-azabicyclo[3.1.0]hexane hydrochloride

A solution of 9.0 g. of cis-1-phenyl-1,2-cyclopropanedicarboxylic acid (J. Med. Chem. 24:481) in 100 ml. of tetrahydrofuran is added to 180 ml. of 1 M borane-tetrahydrofuran at 0° C., under nitrogen over 15 minutes. The solution is kept at room temperature for 30 minutes and then is refluxed for 4 hours. After cooling the reaction mixture in ice, 60 ml. of 6 N hydrochloric acid is added and the tetrahydrofuran is removed under reduced pressure. The aqueous residue is made basic with sodium hydroxide and extracted with ether. The extract is dried over potassium carbonate and the filtered solution is evaporated to give 7.7 g. of cis-1-phenyl-1,2-cyclopropanedimethanol.

A solution of 6.0 g. of the above diol in 335 ml. of dichloromethane and 14 ml. of triethylamine is cooled to −10° C. and to this is added 8.45 g. of methanesulfonyl chloride over 15 minutes. This is stirred at room temperature for 30 minutes and is washed with cold dilute hydrochloric acid, then with cold water and finally with 10% sodium bicarbonate solution. The organic solution is dried over magnesium sulfate, and the filtered solution is evaporated to give 8.40 g. of the dimethanesulfonate as a pale yellow oil. A solution of this oil in 100 ml. of tetrahydrofuran is combined with 1.0 g. of sodamide and this mixture is refluxed and filtered. Evaporation of the solution gives 1-phenyl-3-azabicyclo[3.1.0]hexane as a colorless liquid. Conversion of this amine to the hydrochloride with ethanolic hydrogen chloride gives 1-phenyl-3-azabicyclo[3.1.0]hexane hydrochloride. When recrystallized from acetonitrile, the product is obtained as colorless crystals, m.p. 166°–167° C.

EXAMPLE 39

1(m-Chlorophenyl)-3-methyl-3-azabicyclo[3.1.0]hexane hydrochloride

To a solution of 18.7 g. of 1-(m-chlorophenyl-1,2-cyclopropanedicarboximide in 100 ml. of anhydrous dimethylformamide is added 5.0 g. of sodium hydride (54% in mineral oil) over 15 minutes. The mixture is stirred for 30 minutes and then 10 ml. of methyliodide are added over 5 minutes. The mixture is allowed to stand 15 minutes, heated on a steam bath for 15 minutes, cooled and poured into 250 ml. of water. The solid is collected, washed with petroleum ether and air dried, giving 1-(m-chlorophenyl)-N-methyl-1,2-cyclopropanedicarboximide.

To a stirred solution of 5.0 g. of this imide in 125 ml. of benzene under nitrogen is added 30 ml. of Vitride ® (70% benzene solution) over 10 minutes. The mixture is refluxed for 5 hours, cooled and 60 ml. of 10N sodium hydroxide are cautiously added. The organic layer is washed with water, dried over magnesium sulfate and evaporated under reduced pressure to an oil. This oil is dissolved in 250 ml. of ether, saturated with hydrogen chloride, the solid is collected and crystallized from acetonitrile, giving the desired product as colorless crystals, m.p. 180°–182° C.

EXAMPLE 40

1-(p-Chlorophenyl)-3-ethyl-3-azabicyclo[3.1.0]hexane

Using the method of Example 15, 1-(p-chlorophenyl)-3-azabicyclo[3.1.0]hexane (Example 1) is reacted with acetyl chloride to give 3-acetyl-1-(p-chlorophenyl)-3-azabicyclo[3.1.0]hexane and then is converted to 1-(p-chlorophenyl)-3-ethyl-3-azabicyclo[3.1.0]hexane which is obtained as a brown oil.

EXAMPLE 41

3-[4,4-bis(p-Fluorophenyl)butyl]-1-phenyl-3-azabicyclo[3.1.0]hexane Fumarate A mixture of sodium hydride and 1-phenyl-1,2-cyclopropanedicarboximide (U.S. Pat. No. 3,166,571) in dry N,N-dimethylformamide is stirred until hydrogen evolution ceases. To this is added 1-chloro-4,4-bis(4-fluorophenyl)butane and the mixture is stirred for 20 hours at room temperature and then is heated briefly at 100° C. The mixture is combined with water and extracted with ether and the extract is evaporated to give N-[4,4-bis(p-fluorophenyl)butyl]-1-phenyl-1,2-cyclopropanedicarboximide as a colorless glass.

Reduction of the above compound as in Example 39 and the combination of the base with fumaric acid gives 3-[4,4-bis(p-fluorophenyl)butyl-1-phenyl-3-azabicyclo[3.1.0]hexane fumarate as colorless crystals, m.p. 153°–155° C.

In the above manner 1-(p-chlorophenyl)-1,2-cyclopropanedicarboximide (U.S. Pat. No. 3,344,026) is converted to N-[4,4-bis(p-fluorophenyl)butyl]-1-(p-chlorophenyl)-1,2-cyclopropanedicarboximide. This compound is reduced as in Example 23 and the base is combined with fumaric acid to give 3-[4,4-bis(p-fluorophenyl)butyl]-1-(p-chlorophenyl)-3-azabicyclo[3.1.0]hexane fumarate as colorless crystals, m.p. 152°–154° C.

EXAMPLE 42

3-[3-(p-Fluorobenzoyl)propyl]-1-phenyl-3-azabicyclo[3.1.0]hexane hydrochloride A mixture of 15.9 g. of 1-phenyl-3-azabicyclo[3.1.0]hexane, 20.1 g. of -chloro-p-fluorobutyrophenone and 10 mg. of potassium iodide in 100 ml. of toluene is refluxed for 24 hours. Filtration gives 11.6 g. of 1-phenyl-3-azabicyclo[3.1.0]hexane hydrochloride. Evaporation of the filtrate gives a brown oil which is combined with 2N hydrochloric acid and chloroform. The crystals which form in the chloroform layer are collected by filtration and recrystallized from ethanol to give 3.10 g. of 3-[3-(p-fluorobenzoyl)propyl]-1-phenyl-3-azabicyclo[3.1.0]hexane hydrochloride as pale tan crystals, m.p. 151°–153° C.

EXAMPLE 43

1-(m-Methoxyphenyl)-3-azabicyclo[3.1.0]hexane hydrochloride

Methyl-m-methoxymandelate is reacted with phosphorous tribromide by the method of I. P. Beletskaya, Zh. Obshch. Khim. 34: 321(1964) to give methyl bromo-(m-methoxyphenyl)acetate as pale yellow liquid, and used below (without further purification).

In a like manner the following mandelate esters can be converted to the corresponding bromoesters:

| Mandelate ester | Bromoester |
| --- | --- |
| ethyl(p-hexylmandelate | ethyl bromo-(p-hexylphenyl)acetate |
| ethyl(p-isopropyl)mandelate | ethyl bromo-(p-cumyl)acetate |
| methyl(m-methyl)mandelate | methyl bromo-(m-tolyl)acetate |

| Mandelate ester | Bromoester |
|---|---|
| methyl(o-methyl)-mandelate | methyl bromo-(o-tolyl)acetate |
| methyl(3',4'-dimethyl)mandelate | methyl bromo-(3,4-dimethylphenyl)acetate |

A mixture of 37.0 g. of dimethyl 1-(m-methoxyphenyl)-1,2-cyclopropanedicarboxylate [prepared by the method of Example 5 from methyl bromo-(m-methoxyphenyl)acetate and methyl acrylate], 20 g. of potassium hydroxide and 200 ml. of 1:1 water-methanol mixture is refluxed 16 hours and the methanol is removed by concentrating. Concentrated hydrochloric acid is added in incremental portions until the pH is one. The mixture is extracted three times with ether, dried and concentrated to give cis-1-(m-methoxyphenyl)-1,2-cyclopropanedicarboxylic acid as a pale yellow gum.

A 34.7 g. portion of this diacid, 12 g. of urea and 750 ml. of xylene is refluxed and stirred for 5 hours. The mixture is cooled, and the supernatant solution is decanted and filtered through magnesium silicate. The filtrate is concentrated under reduced pressure to give a solid which is recrystallized from ethanol to give 1-(m-methoxyphenyl)-1,2-cyclopropanedicarboximide.

A 3.0 g. portion of the above product is mixed with 75 ml. of benzene and 20 ml. of Vitride ® is added over a 5 minute period with stirring. After stirring for one-half hour and refluxing for one hour the mixture is cooled and 20 ml. of 10 N sodium hydroxide is added, followed by saturated sodium chloride. The organic layer is washed with water and then is dried over magnesium sulfate, filtered and evaporated to an oil. The oil is dissolved in ether and hydrogen chloride gas is bubbled in. The solid which forms is recrystallized from acetonitrile to give 1-(m-methoxyphenyl)-3-azabicyclo[3.1.0]hexane hydrochloride as colorless crystals, m.p. 150°–152° C.

EXAMPLE 44

1-(m-Hydroxyphenyl)-3-methyl-3-azabicyclo[3.1.0]hexane hydrochloride 1-(m-Methoxyphenyl)-3-methyl-3-azabicyclo[3.1.0]hexane hydrochloride is combined with sodium hydride and ethanethiol in N,N-dimethylformamide as in Example 36 to give 1-(m-hydroxyphenyl)-3-methyl-3-azabicyclo[3.1.0]hexane hydrochloride, m.p. 180°–181° C.

EXAMPLE 45

1-[(p-Methoxymethyl)phenyl]-3-azabicyclo[3.1.0]hexane hydrochloride

A mixture of 2.48 g. of cis-dimethyl-1-(p-tolyl)-1,2-cyclopropanedicarboxylate (U.S. Pat. No. 4,131,611, Ex. 36), 1.78 g. of N-bromosuccinimide and 5 mg. of azabisisobutyronitrile in 50 ml. of carbon tetrachloride is irradiated with a 500 watt tungsten lamp for 2 hours. Filtration and evaporation of the filtrate gives cis-dimethyl-1-(-bromo-p-tolyl)-1,2-cyclopropanedicarboxylate as tan crystals which is used in the subsequent transformation without further purification.

The above benzylic bromide is stirred with a methanolic solution of sodium methoxide for 2 hours and then is refluxed for 3 hours, then the methanol is evaporated. The residue is partitioned between water and dichloromethane and the organic solution is evaporated to give cis-dimethyl-1-[(p-methoxymethyl)phenyl]-1,2-cyclopropanedicarboxylate as a dark oil which is used in the subsequent preparation without further purification.

The preceeding diester is hydrolyzed with ethanolic potassium hydroxide as in Example 5 to give cis-1-[(p-mmethoxymethyl)phenyl]-1,2-cyclopropanedicarboxylic acid as a brown oil.

The preceeding dicarboxylic acid is refluxed with urea in xylene as in Example 5 to give 1-[(p-methoxymethyl)phenyl]-1,2-cyclopropanedicarboximide as colorless crystals.

The preceeding imide is reduced with boranetetrahydrofuran as in Example 23 to give 1-[(p-methoxymethyl)phenyl]-3-azabicyclo[3.1.0]hexane hydrochloride.

EXAMPLE 46

1-(p-Tolyl)-3-azabicyclo[3.1.0]hexane

A mixture of 3-(p-tolyl)-3-pyrroline, methylene iodide, and powdered copper in a molar ration of 1:2:4 is heated in benzene for about 50 hours. Filtration and evaporation of the solution gives 1-(p-tolyl)-3-azabicyclo[3.1.0]hexane.

EXAMPLE 47

1-(3,4,5-Trimethoxyphenyl)-3-azabicyclo[3.1.0]hexane hydrochloride 1-(3,4,5-Trimethoxyphenyl)-1,2-cyclopropanedicarboximide is prepared from 1-(3,4,5-trimethoxyphenyl)-1,2-cyclopropanedicarboxylic acid by the general procedures described herein.

A mixture of 458 mg. of this imide and 10 ml. of Vitride ® (70% benzene solution) in benzene is stirred at room temperature for 2 hours, cooled in an ice bath and 10 ml. of 5 N sodium hydroxide are added dropwise. The mixture is partitioned between 2.5 ml. of ether and 2.5 ml. of water. The ether layer is washed with water, dried, made acidic with ethanolic hydrogen chloride and the solid is collected, giving 150 mg. of the desired product, m.p. 204°–206° C.

EXAMPLE 48

1-(p-Aminophenyl)-3-azabicyclo[3.1.0]hexane dihydrochloride

A mixture of 2.51 g. of 1-(p-nitrophenyl)-1,2-cyclopropanedicarboximide and 100 mg. of palladium on carbon catalyst is hydrogenated in 50 ml. of methanol in a Parr shaker. When hydrogen uptake is complete the mixture is filtered through diatomaceous earth. The filter cake is washed with boiling methanol which is then evaporated, giving 2.5 g. of 1-(p-aminophenyl)-1,2-cyclopropanedicarboximide as a red solid. This was reduced with Vitride ® in benzene, as in Example 1, to give 1-(p-aminophenyl)-3-azabicyclo[3.1.0]hexane dihydrochloride as a tan solid, m.p. 205°–207° C.

EXAMPLE 49

1-(p-tert.-Butylphenyl)-3-azabicyclo[3.1.0]hexane hydrochloride

A solution of 28 g. of methyl-p-tert.-butylphenyl acetate and 25.1 g. of N-bromosuccinimide in 350 ml. of carbon tetrachloride plus one drop of hydrogen bromide is stirred and refluxed for 4 hours. The mixture is filtered and the filtrate is slurried with 25 g. of potassium carbonate, then refiltered. This filtrate is evaporated under reduced pressure to an oil which is distilled giving 23.2 g. of a pale straw-colored oil (b.p. 104°–110° C./0.03 mm).

To a slurry of 3.6 g. of sodium hydride (50% in oil) in 200 ml. of ether is added, under argon, 0.2 ml. of absolute methanol. To this is added a mixture of 21 g. of the straw-colored oil, 12.7 g. of methyl acrylate and one ml. of absolute methanol over a period of ½ hour. This mixture is stirred overnight with the addition of one ml. of absolute methanol and one gram of sodium methoxide. The reaction is decomposed by adding cautiously 5 ml. of ethanol, then stirred for one hour and 50 ml. of water are added. The organic layer is washed with water, dried and evaporated to a dark oil which is distilled giving 14.4 g. of 1-(p-tert.-butylphenyl)-1,2-cyclopropanedicarboxylic acid, dimethyl ester as a colorless oil.

A mixture of 12.1 g. of the above ester, 10 g. of potassium hydroxide, 75 ml. of methanol and 75 ml. of water is stirred for 20 hours, refluxed for 4 hours, evaporated to ⅓ volume and extracted with ether. The aqueous portion is made acidic with concentrated hydrochloric acid, the solid is collected, washed with water and air dried, giving 10.9 g. of 1-(p-tert.-butylphenyl)-1,2-cyclopropanedicarboxylic acid as crystals.

A mixture of 10 g. of the above acid and 35 g. of urea in 250 ml. of xylene is refluxed for 20 hours, evaporated under reduced pressure, combined with water and the solid is collected and recrystallized from ethyl acetate-hexane, giving 3.4 g. of 1-(p-tert.-butylphenyl)-1,2-cyclopropanedicarboximide as colorless crystals.

To 3.0 g. of the above imide in 70 ml. of benzene is added 20 ml. of Vitride ® over 5 minutes with stirring. The mixture is refluxed for 6 hours with the addition of Vitride ®, then cooled and decomposed with 30 ml. of 10N sodium hydroxide. The aqueous portion is extracted with ether. The extracts are combined, washed with water, dried, and evaporated to an oily residue. The residue is dissolved in ether, saturated with hydrogen chloride gas and the solid is collected and crystallized from acetonitrile-methanol, giving 1.10 g. of the desired product as pink crystals, m.p. 266°–267° C.

EXAMPLE 50

3-Cyclopropylmethyl)-1-p-tolyl-3-azabicyclo[3.1.0]hexane hydrochloride

A 7.7 g. portion of 1-(p-tolyl)-3-azabicyclo[3.1.0]hexane hydrochloride is dissolved in 100 ml. of 5 N sodium hydroxide. The mixture is extracted with dichloromethane. The extracts are combined, washed with water, dried, filtered and concentrated to dryness. The residual oil is triturated with hexane, filtered and evaporated giving 7.8 g. of 1-(p-tolyl)-3-azabicyclo[3.1.0]hexane as an oil.

A mixture of 7.8 g. of this amine, 6.8 g. of cyclopropylmethyl bromide, 9.4 g. of sodium carbonate and 60 ml. of toluene is refluxed for 18 hours and then cooled. A 10 ml. portion of 5 N sodium hydroxide is added and after mixing the aqueous layer is extracted twice with toluene. The combined extracts are washed with water, dried, filtered and concentrated to an oil. This oil is treated with 25 ml. of 3 N ethanolic hydrogen chloride and ether to give a solid. Recrystallization from acetonitrile gives 6.1 g. of the desired product, m.p. 187°–189° C.

EXAMPLE 51

4-Methyl-1-p-tolyl-3-azabicyclo[3.1.0]hexane hydrochloride

To 12.0 g. of 1-(p-tolyl)-1,2-cyclopropanedicarboximide in 90 ml. of tetrahydrofuran is carefully added 42 ml. of 2.9 M methyl magnesium bromide in ether. The mixture is stirred for 48 hours, 150 ml. of water, 120 ml. of 1 N hydrochloric acid and 300 ml. of chloroform are added and the mixture is shaken. The aqueous layer is reextracted with 300 ml. of chloroform. The chloroform layers are combined, washed with water, dried and concentrated. The residue is treated with 50 ml. of ether to give 4-hydroxy-4-methyl-2-oxo-1-p-tolyl-3-azabicyclo[3.1.0]hexane as colorless crystals.

A 3.8 g. portion of this solid is dissolved in 100 ml. of tetrahydrofuran. To this is added with stirring under nitrogen 75 ml. of 1 M borane in tetrahydrofuran over a 20 minute period. The reaction mixture is stirred for 1.5 hours, heated under reflux for 4 hours, stirred at room temperature overnight and then cooled in an ice bath while 50 ml. of 6 N hydrochloric acid are carefully added with stirring. The tetrahydrofuran is removed by distillation on a steam bath. The remainder of the reaction mixture is cooled in an ice bath and 30 g. of sodium hydroxide pellets are added portionwise with stirring. A 25 ml. portion of water is added and the mixture is extracted twice with chloroform. The chloroform extracts are combined, washed with water, dried, filtered and concentrated to an oil. This oil is dissolved in ether, acidified with 8 ml. of 3.55 N ethanolic hydrogen chloride, the solid is collected and recrystallized from hot acetonitrile giving 2 g. of the desired product, m.p. 155°–157° C.

EXAMPLE 52

3,4-Dimethyl-1-p-tolyl-3-azabicyclo[3.1.0]hexane hydrochloride

4-Hydroxy-4-methyl-2-oxo-1-p-tolyl-3-azabicyclo[3.1.0]hexane is prepared as described in Example 51. To a solution of 4.5 g. of the above hexane derivative in 120 ml. of tetrahydrofuran is added, with stirring under nitrogen in an ice bath 100 ml. of 1 M borane in tetrahydrofuran. The mixture is stirred ½ hour, heated and stirred under reflux for 3½ hours, then stirred overnight at room temperature. The mixture is then stirred and cooled in an ice bath as 70 ml. of 6 N hydrochloric acid are cautiously added. The tetrahydrofuran is distilled off and 25 ml. of water and 42 g. of sodium hydroxide pellets are added portionwise. The alkaline phase is extracted three times with chloroform. The extracts are combined, washed with water, dried, filtered and concentrated to an oil. This oil is dissolved in 200 ml. of ether and acidified with 12 ml. of 3.55 N ethanolic hydrogen chloride. The solid is collected, treated with 30 ml. of 1 N sodium hydroxide and extracted twice with ether. The ether extracts are combined, washed with water, dried, filtered and concentrated, giving 3.1 g. of 4-methyl-1-p-tolyl-3-azabicyclo[3.1.0]hexane as a yellow oil.

A mixture of this oil, 35 ml. of 97% formic acid and 30 ml. of 37% formaldehyde is heated with stirring under reflux for 3½ hours. The mixture is concentrated under reduced pressure to a white paste and treated with 50 ml. of 5 N sodium hydroxide and sufficient ether to produce solution. The aqueous phase is separated and extracted with ether. The ether solutions are combined, washed with saline, dried, filtered and acidified with 6 ml. of 3.55 N ethanolic hydrogen chloride. The resulting solid is recrystallized from 100 ml. of hot acetonitrile, giving 1.8 g. of the desired product, m.p. 251°–253° C.

EXAMPLE 53

4'-(3-Azabicyclo[3.1.0]hex-1-yl)-acetophenone hydrochloride

A 3 g. portion of 1-phenyl-3-azabicyclo[3.1.0]hexane hydrochloride is added to a cold (0° C.) mixture of 2.8 g. of acetyl chloride and 6.9 g. of aluminum chloride in 30 ml. of dichloromethane, and the reaction is stirred for 15 minutes. The mixture is then brought to room temperature, stirred overnight and carefully poured onto ice. This mixture is extracted twice with dichloromethane, and the extracts are combined, dried, filtered and concentrated to an oil. This oil is dissolved in a minimum of dichloromethane and treated with an excess of ether to give a solid which is collected, washed with ether and dried. Recrystallization from acetonitrile gives 500 mg. of the desired product, m.p. 195°-197° C.

EXAMPLE 54

1-[(3,4-Methylenedioxy)phenyl]-3-azabicyclo[3.1.0]hexane hydrochloride

A mixture of 105 g. of potassium cyanide, 138 g. of piperonal and 160 ml. of water is prepared in a 2 liter three-necked flask. Slowly, over 25 minutes there is added 225 ml. of a saturated solution of sodium bisulfite with the addition of sufficient ice to maintain the reaction temperature at 25°-30° C. The lower phase is separated and then is added with stirring and ice-bath cooling to 130 ml. of concentrated hydrochloric acid. The mixture is stirred overnight, 250 ml. of chloroform and 100 ml. of water are added and the mixture is shaken in a separatory funnel. The aqueous-acid layer is concentrated, the solid is collected, washed with water, then ether and dried giving 5.2 g. of white crystals. A 2.6 g. portion of these crystals is dissolved in 50 ml. of methanol and hydrogen chloride gas is bubbled in for 15 minutes. After standing for 2 hours the solution is concentrated to an oil. A 50 ml. portion of chloroform and 25 ml. of saturated sodium bicarbonate are added and the mixture is shaken in a separatory funnel. The chloroform layer is separated and the aqueous layer is reextracted twice with fresh chloroform. The chloroform solutions are combined, washed with water, dried, filtered and concentrated to an oil which is distilled in a Kugelrohr apparatus (b.p. 110° C./0.025 mm.) giving an oil which is 1-(3,4-methylenedioxyphenyl)-hydroxy methyl acetate.

A solution of 8.4 g. of this hydroxy ester in 40 ml. of chloroform is added over a period of ½ hour to a stirred, chilled solution of 2.4 ml. of phosphorous tribromide in 20 ml. of chloroform. The mixture is stirred overnight, quenched with ice and the chloroform layer is washed with water, dried, filtered and evaporated to give 10.3 g. of bromo(3,4-methylenedioxyphenyl)-acetic acid methyl ester as a yellow oil.

To a stirred suspension of 21.2 g. of sodium hydride (50% in mineral oil) in 2.2 liters of ether is added a mixture of 133.3 g. of bromo(3,4-methylenedioxyphenyl)-acetic acid methyl ester (prepared as described above), 42.1 g. of methyl acrylate and 6 ml. of methanol over a period of 20 minutes. The mixture is then stirred for 48 hours, one ml. of methanol is added and stirring is continued for 1.5 hours. A 13 ml. portion of methanol is added and the mixture is stirred for 3 days. The reaction mixture is divided into two equal portions. Each half is washed with 175 ml. of water. The water washes are combined, saturated with sodium chloride and reextracted with 500 ml. of ether. All of the ether phases are combined, washed with 300 ml. of water, dried, filtered and concentrated to an oil. The mineral oil is separated and the remaining oil is distilled at 145°-150° C./0.15 mm. in a Kugelrohr apparatus giving 76.1 g. of 1-(3,4-methylenedioxyphenyl)-1,2-cyclopropanedicarboxylic acid, dimethyl ester.

A mixture of 74 g. of potassium hydroxide dissolved in 750 ml. of water is stirred under reflux for 6 hours. The methanol is removed under reduced pressure on a steam bath. The aqueous residue is extracted with ether and then acidified with 200 ml. of 6 N hydrochloric acid. The aqueous phase is extracted with chloroform, and the chloroform extracts are combined with the ether extract and dried, filtered and concentrated to give crystals which are collected, washed with ethyl acetate, then hexane and dried. Recrystallization from acetonitrile gives 1-(3,4-methylenedioxyphenyl)-1,2-cyclopropanedicarboxylic acid.

A mixture of 22.9 g. of the above diacid, 9.1 g. of urea and 150 ml. of xylene is stirred and heated under reflux for 18 hours. The solution is decanted and washed with 180 ml. of 10% sodium carbonate solution. The residual gum is extracted with chloroform. The combined extracts are evaporated under reduced pressure to give a solid. Recrystallization from ethyl acetate-hexane gives 12.9 g. of 1-(3,4-methylenedioxyphenyl)-1,2-cyclopropanedicarboximide.

A 7.4 g. portion of the above imide is converted to the desired product using Vitride®, as previously described to give colorless crystals, m.p. 210°-212° C.

EXAMPLE 55

4-Ethyl-1-p-tolyl-3-azabicyclo[3.1.0]hexane hydrochloride

To 4 g. of 1-(p-tolyl)-1,2-cyclopropanedicarboximide dissolved in 30 ml. of tetrahydrofuran is slowly added, with stirring, 14 ml. of 2.94 M ethyl magnesium bromide in ether. The mixture is stirred overnight, then treated with 50 ml. of water, and 100 ml. of chloroform. Mixing produces three layers. The chloroform layer is separated and saved. The aqueous and emulsion phases are combined, acidified with 40 ml. of 1 N hydrochloric acid and then extracted with chloroform. The chloroform solutions are combined and washed with water. The chloroform layer is dried, filtered and concentrated to an oil which crystallizes on combination with ether. Recrystallization from ether gives 1.8 g. of 4-ethyl-4-hydroxy-p-tolyl-3-azabicyclo[3.1.0]hexan-2-one.

To a solution of 1.4 g. of 4-ethy-4-hydroxy-p-tolyl-3-azabicyclo[3.1.0]hexan-2-one in 35 ml. of tetrahydrofuran is added, with stirring, 27 ml. of 1 M borane in tetrahydrofuran. The mixture is stirred for one hour, refluxed for 4 hours, chilled and then carefully acidified with 20 ml. of 6 N hydrochloric acid. The solvent is removed on a steam bath and the chilled residue is made basic by the portionwise addition of 12 g. of sodium hydroxide pellets and ice. This alkaline mixture is extracted with chloroform, and the extracts are washed with water, dried, and evaporated under reduced pressure to give an oil. The oil is dissolved in 100 ml. of ether, acidified with 3 ml. of 3.55 N alcoholic hydrogen chloride and chilled. Evaporation under reduced pressure gives a gum which is crystallized by trituration with ethyl acetate-ether. Recrystallization from acetonitrile-ether gives 375 mg. of the desired product as colorless crystals, m.p. 153°-154° C.

EXAMPLE 56

(−)-1-(p-Chlorophenyl)-α-methyl-3-azabicyclo[3.1.0-]hexane-3-acetanilide hydrochloride A mixture of 3.5 g. of (−)-1-(p-chlorophenyl)-3-azabicyclo[3.1.0]hexane (U.S. Pat. No. 4,131,611), 4.6 g. of 2-bromopropionanilide, 3.7 g. of sodium carbonate and 75 ml. of toluene is stirred and refluxed overnight. The mixture is diluted with 25 ml. of water and 5 ml. of 5 N sodium hydroxide and mixed. The alkaline aqueous layer is extracted with toluene. The toluene layers are combined, washed with water, dried, filtered and concentrated to an oil. The oil is triturated in 50 ml. of ether and filtered. The filtrate is acidified with 6 ml. of 3.55 N alcoholic hydrogen chloride and scratched and resuspended in ether repeatedly until crystalline. The solid is collected, washed with ether, dried, heated to solution in 25 ml. of acetonitrile, filtered and cooled, giving 1.2 g. of the desired product, m.p. 227°–228° C.

EXAMPLE 57

4'-(3-Azabicyclo[3.1.0]hex-1-yl)-benzophenone hydrochloride

A mixture of 12.9 g. of aluminum chloride and 9.7 g. of benzoyl chloride in 55 ml. of dichloromethane is stirred at −10° C. To this is added 5.6 g. of 1-phenyl-3-azabicyclo[3.1.0]hexane over a period of 10 minutes while the temperature is maintained at −10° C. to −5° C. The reaction is then stirred at 0° C. for 10 minutes, and then at room temperature for two days. The mixture is carefully poured onto ice and then extracted with dichloromethane. The extract is dried, filtered, and then concentrated to 25 ml. and diluted with ether. The resultant solid is collected, washed with ether, dried and recrystallized from acetonitrile to give 2.0 g. of the desired product, m.p. 171°–173° C.

EXAMPLE 58

4'-(3-Azabicyclo[3.1.0]hex-1-yl)-propiophenone hydrochloride

A mixture of 5.6 g. of 1-phenyl-3-azabicyclo[3.1.0-]hexane hydrochloride, 12.9 g. of aluminum chloride and 6.2 g. of propionyl chloride in 55 ml. of dichloromethane is reacted as described in Example 57, to give 4.5 g. of the desired product, m.p. 191°–193° C.

EXAMPLE 59

1-(α-Phenyl-p-tolyl)-3-azbicyclo[3.1.0]hexane

Amalgamated zinc is prepared using 4.6 g. of mossy zinc, 460 mg. of mercuric chloride, 6.3 ml. of concentrated hydrochloric acid and 7.2 ml. of water. This mixture is stirred for one hour, the aqueous portion is decanted and then 3.5 ml. of water, 6.3 ml. of concentrated hydrochloric acid and 1.7 g. of 4-(3-azabicyclo[3.1.0]hex-1-yl)-benzophenone hydrochloride are added. The mixture is heated under reflux for 3 hours, 1.5 ml. of concentrated hydrochlorid acid is added and refluxing is continued for 3 hours. The mixture is diluted with 50 ml. of water, heated and filtered while hot. The residue is washed with dichloromethane and hot water. The filtrate and wash are combined and mixed with 25 ml. of 5 N sodium hydroxide and then filtered. The filtrate is extracted with dichloromethane, and the extract is evaporated to an oil which is diluted with 100 ml. of ether and combined with 2 ml. of 3.55 N ethanolic hydrogen chloride. The resulting solid is collected and recrystallized from acetonitrile, to give 345 mg. of the desired product, m.p. 153°–155° C.

EXAMPLE 60

1-(p-Isopropoxyphenyl)-3-azabicyclo[3.1.0]hexane hydrochloride

To a stirred mixture of 2.0 g. of 1-(p-hydroxyphenyl)-3-azabicyclo[3.1.0]hexane-3-carboxaldehyde (U.S. Pat. No. 4,131,611) and 1.4 g. of potassium carbonate in 50 ml. of ethanol, is added 3.76 ml. of isopropyl bromide in 20 ml. of absolute ethanol. This mixture is refluxed for 4 hours, then filtered and evaporated to an oil. The oil is crystallized from dichloromethane-hexane, to give 1.74 g. of 1-(p-isopropoxyphenyl)-3-azabicyclo[3.1.0]hexane-3-carboxaldehyde.

A solution of 1.62 g. of the above derivative in a mixture of 36.7 ml. of ethanol and 14.7 ml. of 5 N sodium hydroxide is heated on a steam bath for 2 hours. The ethanol is removed under reduced pressure and the aqueous residue is extracted with ether. The extract is dried, filtered and combined with an excess of ethanolic hydrogen chloride. The solid is collected and recrystallized from acetonitrile, giving 1.15 g. of the desired product, m.p. 176°–178° C.

EXAMPLE 61 p-(3-Azabicyclo[3.1.0]hex-1-yl)-benzyl alcohol

A mixture of 11 g. of 1-p-tolyl-1,2-cyclopropanedicarboximide, 450 ml. of chlorobenzene, 20 mg. of azobisisobutyronitrile and 10.8 g. of N-bromosuccinimide is stirred and heated on a steam bath with irradiation from a 500 watt photofloodlamp for 45 minutes. The chlorobenzene is removed on a steam bath under reduced pressure and the oily residue is dissolved in 300 ml. of dichloromethane. The solution is washed with water, dried, filtered and evaporated under reduced pressure. The residue is crystallized from ethyl acetate-hexane to give 1-(p-dibromomethylphenyl)-1,2-cyclopropanedicarboximide.

An 8.5 g. portion of this imide in a mixture of 850 ml. of acetone and 85 ml. of water is stirred and 17 g. of silver nitrate dissolved in 170 ml. of water is added over a period of 5 minutes. The reaction mixture is stirred at steam bath temperature for 5 minutes, filtered through diatomaceous earth and the acetone is removed under reduced pressure. The aqueous layer is chilled to give 1-(p-formylphenyl)-1,2-cyclopropanedicarboximide as colorless crystals.

A 500 mg. portion of this imide is stirred in 15 ml. of toluene and treated with 5.5 ml. of Vitride® (70% benzene solution). The mixture is refluxed for 4 hours, and then cooled in an ice bath. An 8 ml. portion of 10 N sodium hydroxide is carefully added and the layers are separated. The aqueous layer is extracted with dichloromethane and the organic layers are combined, washed with saturated brine, dried, filtered and evaporated under reduced pressure to give an oil. A solution of this oil in ether is treated with alcoholic hydrogen chloride to give the desired product as pink crystals, m.p. 80°–82° C.

EXAMPLE 62

1-(3,4-Dimethylphenyl)-3-azabicyclo[3.1.0]hexane hydrochloride

A mixture of 35.6 g. of dimethyl 1-(3,4-dimethylphenyl)-1,2-cyclopropanedicarboxylate (prepared by the general procedure of Example 43), 21.4 g. of potassium hydroxide, 355 ml. of methanol and 355 ml. of water is refluxed for 6 hours, and then the methanol is distilled off. The residual aqueous solution is washed with ether, and then acidified with 90 ml. of 6 N hydrochloric acid. The resulting solid is collected, dried and recrystallized from acetonitrile to give 1.3 g. of 1-(3,4-dimethylphenyl)-1,2-cyclopropanedicarboxylic acid.

A 9.1 g. portion of 1-(3,4-dimethylphenyl)-1,2-cyclopropanedicarboxylic acid (prepared as described above) and 3.9 g. of urea in 650 ml. of xylene is stirred and refluxed for 20 hours. The mixture is cooled, washed with 10% sodium bicarbonate solution and then with water. The solution is dried, filtered and evaporated. The residue is triturated with hexane to give a solid. Recrystallization from ethyl acetate gives 4.3 g. of 1-(3,4-dimethylphenyl)-1,2-cyclopropanedicarboximide which is then reacted with Vitride®, and the product is converted to 1.2 g. of the desired hydrochloride salt (as described in Example 61), m.p. 176°–178° C.

EXAMPLE 63

1-(p-Diethylaminophenyl)-3-azabicyclo[3.1.0]hexane dihydrochloride

A mixture of 25 g. of 1-(p-nitrophenyl)-1,2-cyclopropanedicarboximide, 25 ml. of acetaldehyde, 10 ml. of acetic acid, one liter of 95% ethanol, and 2 g. of platinum oxide is shaken in a hydrogen atmosphere at 3 atmospheres for 18 hours. Evaporation of the solvents gives a yellow oil. Chromatography of this oil gives 3 g. of 1-(p-diethylaminophenyl)-1,2-cyclopropanedicarboximide as colorless crystals, m.p. 137°–139° C., and 1 g. of 1-(p-ethylaminophenyl)-1,2-cyclopropanedicarboximide crystals, m.p. 197°–199° C.

To a suspension of 3 g. of 1-(p-diethylaminophenyl)-1,2-cyclopropanedicarboxamide in 75 ml. of toluene is added 75 ml. of Vitride® (70% in toluene). This solution is refluxed for 2½ hours, the reaction mixture is cooled, and to this is added 27 ml. of 10 N sodium hydroxide. The organic phase is washed with water, dried over sodium sulfate, and evaporated to give 2.9 g. of an orange oil. This is combined with ethanolic hydrogen chloride to give 2.7 g. of 1-(p-diethylaminophenyl)-3-azabicyclo[3.1.0]hexane dihydrochloride as tan crystals, m.p. 194°–196° C.

In a like manner, Vitride® reduction of 1-(p-ethylaminophenyl)-1,2-cyclopropanedicarboximide gives 1-(p-ethylaminophenyl)-3-azabicyclo[3.1.0]hexane. This is combined with ethanolic fumaric acid to give 1-(p-ethylaminophenyl)-3-azabicyclo[3.1.0]hexane fumarate, m.p. 161°–162° C.

EXAMPLE 64

1-(3,4-dichlorophenyl)-3-Methyl-3-azabicyclo[3.1.0]hexane hydrochloride

By the method of Example 34, 1-(3,4-dichlorophenyl)-3-azabicyclo[3.1.0]hexane hydrochloride (Example 23) is converted to 1-(3,4-dichlorophenyl)-3-methyl-3-azabicyclo[3.1.0]hexane hydrochloride, m.p. 160°–171° C.

EXAMPLE 65

3-Ethyl-1-(p-tolyl)-3-azabicyclo[3.1.0]hexane hydrochloride

A mixture of 7.4 g. of 1-(p-tolyl)-3-azabicyclo[3.1.0]hexane (Example 32), 7.3 g. of ethyl iodide and 8.9 g. of sodium carbonate in 60 ml. of toluene is heated at reflux for 18 hrs. Filtration and evaporation of this mixture gives a residue which is dissolved in ether. Addition of ethanolic hydrogen chloride gives a precipitate which is recrystallized from acetonitrile to give the desired product as colorless crystals, m.p. 175°–176° C.

In a similar manner, 1-(m-chlorophenyl)-3-azabicyclo[3.1.0]hexane (Example 5) gives 3-ethyl-1-(m-chlorophenyl)-3-azabicyclo[3.1.0]hexane hydrochloride as colorless crystals, m.p. 148°–150° C.

In a similar manner, 1-(3,4-dichlorophenyl)-3-azabicyclo[3.1.0]hexane (Example 33) gives 3-ethyl-1-(3,4-dichlorophenyl)-3-azabicyclo[3.1.0]hexane hydrochloride as colorless crystals, m.p. 178°–180° C.

EXAMPLE 66

(−)-3-Methyl-1-phenyl-3-azabicyclo[3.1.0]hexane hydrochloride

To a solution of 18.7 g. of (−)-1-phenyl-1,2-cyclopropanedicarboximide (J. Med. Chem. 24:481) in 100 ml. of anhydrous dimethylformamide is added 5.0 g. of sodium hydride (54% in mineral oil) over 15 minutes. The mixture is stirred for 30 minutes and then 10 ml. of iodomethane is added over 5 minutes. The mixture is allowed to stand for 15 minutes, heated on a steam bath for 15 minutes, cooled and poured into 250 ml. of water. The mixture is filtered and the crystals are washed with petroleum ether and air dried giving (−)-N-methyl-1-phenyl-1,2-cyclopropanedicarboximide.

To a stirred solution of 5.0 g. of (−)-N-methyl-1-phenyl-1,2-cyclopropanedicarboximide in 125 ml. of benzene under nitrogen is added 30 ml. of sodium bis(2-methoxyethoxy)aluminum hydride (70% benzene solution) over 10 minutes. The mixture is refluxed for 5 hours, cooled and 60 ml. of 10 N sodium hydroxide is added cautiously. The organic layer is washed with water, dried over magnesium sulfate and evaporated under reduced pressure to give an amber oil. This oil is dissolved in 250 ml. of ether, saturated with hydrogen chloride and filtered giving colorless crystals. These crystals are recrystallized from acetonitrile giving colorless crystals, m.p. 194°–196° C. $[\alpha]_D CH_3OH = -73°$ C.

EXAMPLE 67

Preparation of Compressed Tablet

| Ingredient | mg./Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 68

Preparation of Compressed Tablet—Sustained Action

| Ingredient | mg./Tablet |
|---|---|
| Active Compound as Aluminum Lake, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

EXAMPLE 69

Preparation of Hard Shell Capsule

| Ingredient | mg./Capsule |
|---|---|
| Active Compound | 0.5–500 |
| Lactose, Spray Dried | qs |
| Magnesium Stearate | 1–10 |

EXAMPLE 70

Preparation of Oral Liquid (Syrup)

| Ingredient | % W/V |
|---|---|
| Active Compound | 0.5–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 71

Preparation of Oral Liquid (Elixir)

| Ingredient | % W/V |
|---|---|
| Active Compound | 0.5–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 72

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

We claim:

1. A compound selected from the group consisting of an optically active compound of the formula:

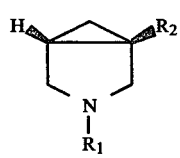

the mirror image isomer thereof, the racemic mixture of the optical isomers and the pharmacologically acceptable acid addition salts thereof wherein $R_1$ is hydrogen or a moiety of the formula:

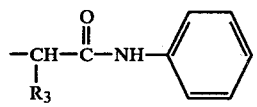

wherein $R_3$ is alkyl($C_1$–$C_3$), $R_2$ is 3,4-methylenedioxyphenyl or a moiety of the formula:

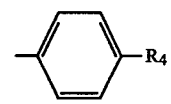

wherein $R_4$ is chloro, bromo, alkanoyl($C_2$–$C_4$), alkylamino ($C_1$–$C_3$), dialkylamino($C_1$–$C_3$), hydroxymethyl, benzyl or benzoyl with the proviso that when $R_1$ is hydrogen then $R_4$ may not be halogen.

2. The racemate according to claim 1 wherein $R_1$ is hydrogen and $R_2$ is para-acetylphenyl; dl-4'-(3-azabicyclo[3.1.0]hex-1-yl)acetophenone hydrochloride.

3. The racemate according to claim 1 wherein $R_1$ is hydrogen and $R_2$ is 3,4-methylenedioxyphenyl; dl-1-(3,4-methylenedioxyphenyl)-3-azabicyclo[3.1.0]hexane hydrochloride.

4. The enantiomer according to claim 1 wherein $R_1$ is α methyl-phenylcarbamoylmethyl and $R_2$ is para-chlorophenyl;1-1-(p-chlorophenyl)-α-methyl-3-azabicyclo[3.1.0]-hexane-3-acetanilide hydrochloride.

5. The racemate according to claim 1 wherein $R_1$ is hydrogen and $R_2$ is para-benzoylphenyl; dl-'4-(3-azabicyclo[3.1.0]hex-1-yl)benzophenone hydrochloride.

6. The racemate according to claim 1 wherein $R_1$ is hydrogen and $R_2$ is para-propionylphenyl; dl-4'-(3-azabicyclo[3.1.0]hex-1-yl)-propiophenone hydrochloride.

7. The racemate according to claim 1 wherein $R_1$ is hydrogen and $R_2$ is para-benzylphenyl; dl-1-(α-phenyl-p-tolyl)-3-azabicyclo[3.1.0]hexane.

8. The racemate according to claim 1 wherein $R_1$ is hydrogen and $R_2$ is para-hydroxymethyl; dl-p-(3-azabicyclo[3.1.0]hex-1-yl)benzyl alcohol.

9. The racemate according to claim 1 wherein $R_1$ is hydrogen and $R_2$ is para-diethylamino; dl-1-(p-diethyl aminophenyl)-3-azabicyclo[3.1.0]hexane dihydrochloride.

10. A method of treating depression in a mammal which comprises administering to said mammal an antidepressant effective amount of a compound of claim 1.

11. A method of treating depression in a mammal which comprises administering to said mammal an antidepressant effective amount of a compound of the formula:

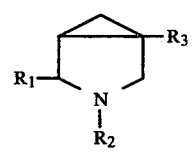

wherein $R_1$ is hydrogen or alkyl($C_1$–$C_3$), $R_2$ is hydrogen, alkyl($C_1$–$C_3$), cyclopropylmethyl, allyl or a moiety of the formula:

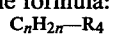

wherein n is 1 or 2 and $R_4$ is phenyl, halophenyl, naphthyl, norbornenyl or adamantyl, $R_3$ is 3,4-methylenedioxyphenyl, 3,4,5-trimethoxyphenyl or a moiety of the formula:

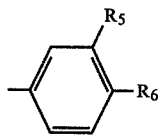

wherein $R_5$ is hydrogen, halogen, hydroxy, alkoxy($C_1$–$C_3$), alkyl($C_1$–$C_3$) or trifluoromethyl, and $R_6$ is hydrogen, halogen, alkoxy($C_1$–$C_3$), alkyl($C_1$–$C_6$), acyl($C_2$–$C_4$), amino, alkylamino($C_1$–$C_3$), dialkylamino($C_1$–$C_3$), hydroxymethyl, trifluoromethyl, phenyl, benzyl or benzoyl; the optical isomers thereof, the racemic mixtures thereof, or the pharmacologically acceptable acid-addition salts thereof.

12. The method according to claim 11 wherein the compound is 1-(p-chlorophenyl)-3-azabicyclo[3.1.0]hexane hydrochloride.

13. The method according to claim 11 wherein the compound is 1-phenyl-3-azabicyclo[3.1.0]hexane.

14. The method according to claim 11 wherein the compound is (+)-1-phenyl-3-azabicyclo[3.1.0]hexane hydrochloride.

15. The method according to claim 11 wherein the compound is 1-(3,4-dichlorophenyl)-3-azabicyclo[3.1.0]hexane hydrochloride.

16. The method according to claim 11 wherein the compound is 1-(m-methoxyphenyl)-3-methylazabicyclo[3.1.0]hexane hydrochloride.

17. The method according to claim 11 wherein the compound is 1-(m-hydroxyphenyl)-3-methyl-3-azabicyclo[3.1.0]hexane hydrochloride.

18. The method according to claim 11 wherein the compound is 1-(p-tolyl)-3-azabicyclo[3.1.0]hexane hydrochloride.

19. The method according to claim 11 wherein the compound is (+)-1-(p-tolyl)-3-azabicyclo[3.1.0]hexane hydrochloride.

20. The method according to claim 11 wherein the compound is 3-methyl-1-(p-tolyl)-3-azabicyclo[3.1.0]hexane hydrochloride.

21. The method according to claim 11 wherein the compound is 1-(p-tolyl)-3-azabicyclo[3.1.0]hexane.

22. The method according to claim 11 wherein the compound is 1-(3,4-dichlorophenyl)-3-methyl-3-azabicyclo[3.1.0]hexane hydrochloride.

23. The method according to claim 11 wherein the compound is 3-ethyl-1-(3,4-dichlorophenyl)-3-azabicyclo[3.1.0]hexane hydrochloride.

24. A composition of matter for the treatment of depression characterized in that said composition contains as an active ingredient an anti-depressant effective amount of a compound of claim 1 in association with a pharmaceutically acceptable carrier.

* * * * *